United States Patent [19]

Teraji et al.

[11] Patent Number: 4,616,015
[45] Date of Patent: Oct. 7, 1986

[54] TRIAZINE DERIVATIVES, AND PHARMACEUTICAL COMPOSITIONS COMPRISING THE SAME

[75] Inventors: Tsutomu Teraji, Osaka; Youichi Shiokawa, Ibaraki; Kazuo Okumura, Sakai; Yoshinari Sato, Takaishi, all of Japan

[73] Assignee: Fujisawa Pharmaceutical Co., Ltd., Osaka, Japan

[21] Appl. No.: 598,685

[22] Filed: Apr. 10, 1984

[30] Foreign Application Priority Data

Apr. 18, 1983 [GB] United Kingdom ............... 8310435

[51] Int. Cl.$^4$ .................. C07D 253/06; A61K 31/53
[52] U.S. Cl. ........................................ 514/242; 544/182
[58] Field of Search .............. 544/112, 182; 424/249; 514/242

[56] References Cited

U.S. PATENT DOCUMENTS

| 4,495,185 | 1/1985 | Brown et al. | 544/182 |
| 4,503,054 | 3/1985 | Brown et al. | 544/182 |
| 4,581,356 | 4/1986 | Teraji et al. | 544/182 |

FOREIGN PATENT DOCUMENTS 0052442 5/1982 European Pat. Off. .

Primary Examiner—John M. Ford
Attorney, Agent, or Firm—Oblon, Fisher, Spivak, McClelland & Maier

[57] ABSTRACT

New triazine derivatives represented by the formula:

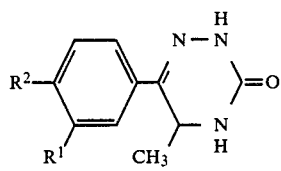

wherein
$R^1$ is hydrogen; halogen or hydrazinocarbonyl(lower)alkyl;
$R^2$ is hydrazino;
  azido;
  halosulfonyl;
  mono- or di(lower)alkylamino;
  mono- or di-(lower alkynylamino;
  pyridylamino;
  lower alkylideneamino substituted by furyl pyridyl or aryl;
  mono- or di-(lower)alkylamino substituted by amino, carboxy, hydroxy, ureido, lower alkoxy, lower alkoxycarbonyl, lower alkoxy(lower)alkoxy, aryl, furyl, pyridyl, phthalimido, or succinimido;
  N-methyl(lower)alkanoylamino;
  N-containing, 5- or 6-membered heterocyclic group optionally substituted by oxo, lower alkyl and/or lower alkoxycalbonyl;
  lower alkoxy substituted by hydroxy and lower alkylamino; or
  a group of the formula

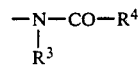

in which
$R^3$ is hydrogen; lower alkyl or ar(lower)alkyl;
$R^4$ is pyridyl; aryl; styryl; alkynyl; lower alkoxycarbonyl; α-hydroxybenzyl; lower alkanoyl; carboxy; or lower alkyl substituted by halogen, amino, hydroxy, carboxy, lower alkanoyl, lower alkanoyloxy, lower alkoxycarbonyl, morpholino, lower alkoxycarbonylamino, 1-methyl-2-oxo-1,2,3,4-tetrahydroquinolyloxy, mono- or di(lower)alkylamino, piperazinyl being substituted with hydroxy(lower)alkyl or furoyl, or pyrrolidino;

and pharmaceutically acceptable salt thereof, which are useful in the treatment of hypertension, thrombosis and ulcer in human beings and animals.

11 Claims, No Drawings

TRIAZINE DERIVATIVES, AND PHARMACEUTICAL COMPOSITIONS COMPRISING THE SAME

The present invention relates to novel triazine derivatives and pharmaceutically acceptable salts thereof. More particularly, it relates to novel, 6-substituted 5-methyl-4,5-dihydro-1,2,4-triazin-3(2H)-one and pharmaceutically acceptable salts thereof which have antihypertensive activity, inhibitory activity on platelet aggregation and antiulcer activity, to processes for preparation thereof, to pharmaceutical composition comprising the same, and to a method of using the same therapeutically in the treatment of hypertension, thrombosis and ulcer in human beings and animals.

Accordingly, one object of this invention is to provide novel, 6-substituted-5-methyl-4,5-dihydro-1,2,4-triazin-3(2H)-one and pharmaceutically acceptable salts thereof, which are useful as an antihypertensive agent, antithrombotic agent and antiulcer drug.

Another object of this invention is to provide processes for preparation of said triazine derivatives and pharmaceutically acceptable salts thereof.

A further object of this invention is to provide pharmaceutical composition comprising, as an active ingredient, said triazine derivative or its pharmaceutically acceptable salt.

Still further object of this invention is to provide a method of using said triazine derivative or its pharmaceutically acceptable salt in the treatment of hypertension, thrombosis and ulcer in human beings and animals.

With regard to the state of the art in this field, for example, the European Patent Publication Number 0052442 describes the following 1,2,4-triazin-3(2H)-one compounds.

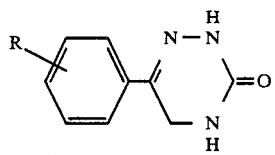

(wherein R is nitro, cyano, amino, methylureido, acetamido, carboxy, lower alkyl, carbamoyl optionally substituted lower alkyl, thiocarbamoyl or morpholinocarbonyl)

It has now been found that certain 6-substituted-5-methyl-4,5-dihydro-1,2,4-triazin-3(2H)-one compounds which have not been described in any of the references have strong and long lasting antihypertensive activity, inhibitory activity on platelet aggregation and antiulcer activity.

The object compounds of the present invention can be represented by the following formula [I].

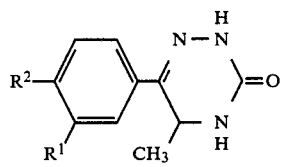

wherein
$R^1$ is hydrogen; halogen or hydrazinocarbonyl(lower)alkyl;

$R^2$ is hydrazino;
azido;
halosulfonyl;
mono- or di-(lower)alkylamino;
mono- or di-(lower)alkynylamino;
pyridylamino;
lower alkylideneamino substituted by furyl, pyridyl or aryl;
mono- or di-(lower)alkylamino substituted by amino, carboxy, hydroxy, ureido, lower alkoxy, lower alkoxycarbonyl, lower alkoxy(lower)alkoxy, aryl, furyl, pyridyl, phthalimido, or succinimido;
N-methyl(lower)alkanoylamino;
N-containing, 5- or 6-membered heterocyclic group optionally substituted by oxo, lower alkyl and/or lower alkoxycarbonyl;
lower alkoxy substituted by hydroxy and lower alkylamino; or
a group of the formula

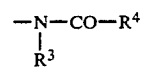

in which
$R^3$ is hydrogen, lower alkyl or ar(lower)alkyl;
$R^4$ is pyridyl; aryl; styryl; alkynyl; lower alkoxycarbonyl; α-hydroxybenzyl; lower alkanoyl; carboxy; or lower alkyl
substituted by halogen, amino, hydroxy, carboxy, lower alkanoyl, lower alkanoyloxy, lower alkoxycarbonyl, morpholino, lower alkoxycarbonylamino, 1-methyl-2-oxo-1,2,3,4-tetrahydroquinolyloxy, mono- or di-(lower)alkylamino, piperazinyl being substituted with hydroxy(lower)alkyl or furoyl, or pyrrolidino.

With regard to the object compound [I], it should be understood that the compounds [I] include all of the possible optical and/or geometrical isomers due to the asymmetric carbon atom(s) and/or double bond(s) in their molecules.

Suitable illustrations and examples of the above definitions are explained in the following.

The term "lower" is intended to mean a group having 1 to 6 carbon atom(s), unless otherwise indicated.

Suitable "halogen" includes bromide, chlorine, iodine and fluorine.

Suitable "lower alkyl" includes straight or branched lower alkyl such as methyl, ethyl, propyl, isopropyl, butyl, isobutyl, sec-butyl, tert-butyl, pentyl, hexyl and the like, and preferably the ones having 1 to 4 carbon atoms.

Suitable "hydrazinocarbonyl(lower)alkyl" is illustrated as "H₂NHNCO-(lower)alkyl", wherein the "lower alkyl" moiety is the same as exemplified above.

Suitable "halosulfonyl" includes fluorosulfonyl, chlorosulfonyl, bromosulfonyl and iodosulfonyl.

Suitable "mono- or di-(lower)alkylamino" includes methylamino, ethylamino, propylamino, isopropylamino, butylamino, pentylamino, hexylamino, N,N-dimethylamino, N,N-diethylamino, N-methyl-N-ethylamino, N,N-dibutylamino, N,N-dipentylamino, N,N-dihexylamino, and the like, wherein more suitable "mono- or di-(lower)alkylamino" is the one containing 1 to 4 carbon atom(s).

These "mono- or di-(lower)alkylamino" group may have substituent(s) selected from amino, carboxy, hydroxy, ureido, lower alkoxy, lower alkoxycarbonyl, lower alkoxy(lower)alkoxy, aryl, furyl, pyridyl, phthalimido, and succinimido as exemplified below.

Suitable "mono- or di-(lower)alkynylamino" includes ethynylamino, 1-propynylamino, 2-propynylamino, 1-butynylamino, 2-butynylamino, 3-butynylamino, -pentynylamino, 5-hexynylamino, di(ethynyl)amino, di(1-propynyl)amino, N-ethynyl-N-(1-propynyl)amino, di(2-propynyl)amino, di(3-butynyl)amino, di(4-pentynyl)amino, di(5-hexynyl)amino and the like.

Suitable "pyridylamino" includes 2-pyridylamino, 3-pyridylamino and 4-pyridylamino.

Suitable "lower alkylideneamino substituted by furyl, pyridyl or aryl" includes furfurylideneamino, 3-furylmethyleneamino, 2-pyridylmethyleneamino, 3-pyridylmethyleneamino, 4-pyridylmethyleneamino, 2-(2-furyl)ethylideneamino, 2-(2-pyridyl)ethylideneamino, 3-(3-furyl)propylideneamino, 2-(3-furyl)propylideneamino, 3-(3-pyridyl)propylideneamino, 4-(2-furyl)-butylideneamino, 3-(2-pyridyl)butylideneamino, 3-(3-furyl)pentylideneamino, 5-(4-pyridyl)pentylideneamino, 6-(2-furyl)hexylideneamino, benzylideneamino and the like.

Suitable "lower alkoxy" and "lower alkoxycarbonyl" are illustrated as "(lower alkyl)—O—" and "(lower alkyl)—O—CO—" respectively, wherein the lower alkyl moiety is the same as exemplified before.

The "lower alkoxy(lower)alkoxy" group is lower alkoxy group substituted by lower alkoxy wherein the lower alkyl moiety is the same as exemplified before.

Suitable "aryl" includes phenyl, tolyl, xylyl, cumenyl, naphthyl, and the like.

Suitable "furyl" includes 2-furyl and 3-furyl.

Suitable "pyridyl" includes 2-pyridyl, 3-pyridyl and 4-pyridyl.

Suitable "N-methyl(lower)alkanoylamino" may includes N-methylformylamino, N-methylacetamido, N-methylpropionylamino, N-methylisopropionylamino, N-methylbutyrylamino, N-methylvalerylamino, N-methylpivaloylamino, N-methylhexanoylamino, and the like.

Suitable "N-containing 5- or 6-membered heterocyclic group" includes unsaturated 5-membered heterocyclic group such as pyrrolyl, pyrazolyl, imidazolyl, triazolyl, tetrazolyl, oxazolyl, isoxazolyl, thiazolyl, isothiazolyl, etc., partially or fully saturated 5-membered heterocyclic group such as pyrrolidinyl, 2-pyrrolinyl, 3-pyrrolinyl, imidazolidinyl, 2-imidazolinyl, pyrazolidinyl, 4,5-dihydropyrazolyl, oxazolidinyl, 4-oxazolinyl, isoxazolidinyl, 3-isoxazolinyl, thiazolidinyl, 4-thiazolinyl, 4-isothiazolinyl, etc., unsaturated 6-membered heterocyclic group such as pyridyl, pyridazinyl, pyrimidinyl, pyrazinyl, etc., partially or fully saturated 6-membered heterocyclic group such as 1,2-, 1,3- or 1,4-dihyropyridyl, 1,2,3,4-tetrahydropyridyl, piperidyl, piperazinyl, hexahydropyrimidinyl, morpholinyl, etc., and the like.

More suitable "N-containing 5- or 6-membered heterocyclic group" is the one having a bond at the N atom such as 1-pyrrolyl, 1-pyrazolyl, 1-triazolyl, 4,5-dihydropyrazol-1-yl, -pyrrolidinyl, morpholino, hexahydropyrimidin-1-yl and the like.

These "N-containing 5- or 6-membered heterocyclic group" may have one or two substituent(s) selected from oxo, lower alkyl and lower alkoxycarbonyl as exemplified before. The heterocyclic group having such substituents may be exemplified 3,5-dimethylpyrazol-1-yl, 4,5-diethoxycarbonyl-1,2,3-triazol-1-yl, 4,5-dihydro-5-oxo-3-methylpyrazol-1-yl, 2-oxo-hexahydropyrimidin-1-yl, and the like.

Suitable "lower alkoxy substituted by hydroxy and lower alkylamino" includes 3-methylamino-2-hydroxypropoxy, 3-dimethylamino-2-hydroxypropoxy, 3-isopropylamino-2-hydroxypropoxy, and the like.

Suitable "ar(lower)alkyl" includes benzyl, phenethyl, tolylmethyl, xylylmethyl, naphthylmethyl, benzhydryl, phenylpropyl, and the like.

Suitable "alkynyl" includes ethynyl, 1-propynyl, 2-propynyl, 1-butynyl, 2-butynyl, 3-butynyl, 4-pentynyl, 5-hexynyl and the like.

Suitable "lower alkanoyl" includes formyl, acetyl, propionyl, butyryl, isobutyryl, valeryl, isovaleryl, pivaloyl, and the like.

Suitable "lower alkanoyloxy" is illustrated as "(lower alkanoyl)—O—" wherein the lower alkanoyl moiety is the same as exemplified above.

Suitable "lower alkoxycarbonylamino" is illustrated as "(lower alkyl)—O—CO—NH—", wherein the lower alkyl moiety is the same as exemplified before.

Suitable "1-methyl-2-oxo-1,2,3,4-tetrahydroquinolyloxy" includes 1-methyl-2-oxo-1,2,3,4-tetrahydroquinolin-8-yloxy, 1-methyl-2-oxo-1,2,3,4-tetrahydroquinolin-7-yloxy and the like.

Suitable "piperazinyl being substituted with hydroxy(lower)alkyl or furoyl" includes 4-hydroxymethylpiperazinyl, 4-(2-hydroxyethyl)piperazinyl, 4-(2-hydroxypropyl)piperazinyl, 3-(2-hydroxyethyl)-piperazinyl, 2-(4-hydroxybutyl)piperazinyl, 4-(2-furoyl)piperazinyl, 2-(3-furoyl)piperazinyl and the like.

Suitable pharmaceutically acceptable salts of the object compound [I] are conventional non-toxic salts and may include an acid addition salt such as an inorganic acid addition salt (e.g., chloride, bromide, sulfate, phosphate, etc.), an organic acid addition salt (e.g., oxalate, maleate, lactate, tartrate, fumarate, methanesulfonate, benzenesulfonate, toluenesulfonate, etc.) or a salt with an amino acid (e.g., arginine salt, aspartic acid salt, glutamic acid salt, etc.), a salt with a base such as alkali metal salt (e.g., sodium salt, potassium salt, etc.), alkaline earth metal salt (e.g. magnesium salt, calucium salt, etc.) and the like.

The object compounds [I] of the present invention can be prepared by the following processes.

Process 1:

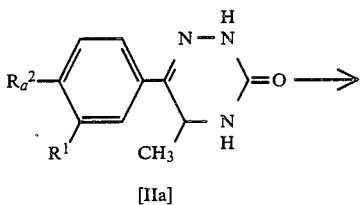

[IIa]

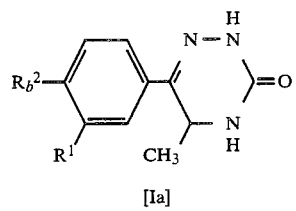

[Ia]

Process 2:

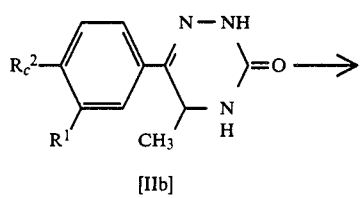
[IIb]
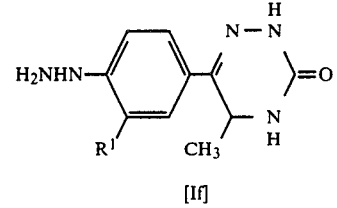
[If]
Process 6:
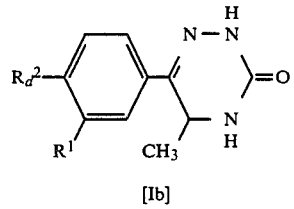
[Ib]
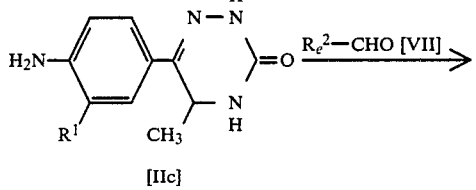
[IIc]
Process 3:
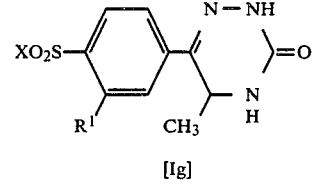
[Ig]
Process 7:
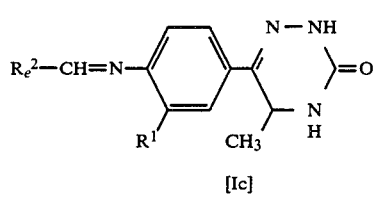
[IIc]
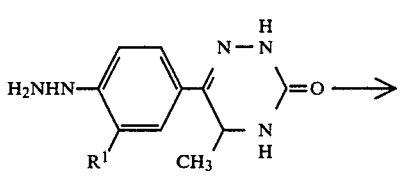
[If]
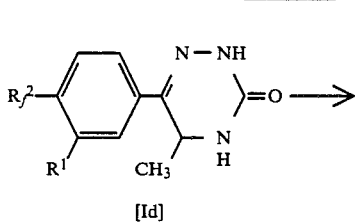
[Ic]
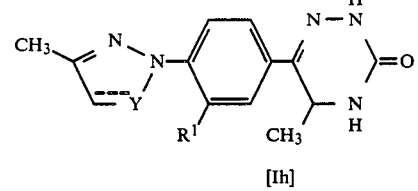
[Ih]
Process 4:
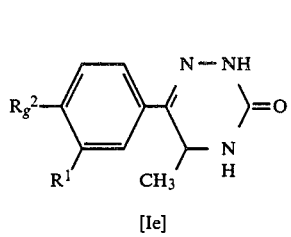
[Id]
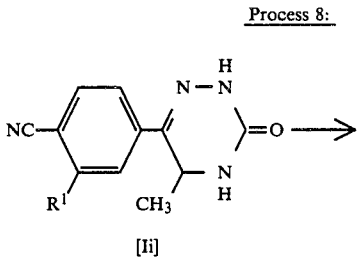
[Ii]
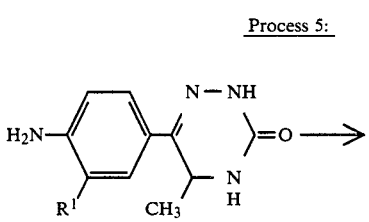
[Ie]
Process 5:
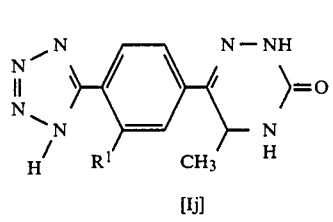
[Ij]
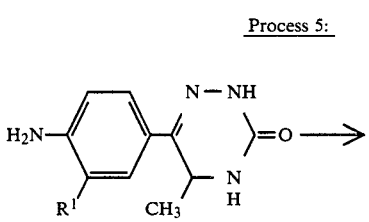
[IIc]
Process 9:

-continued
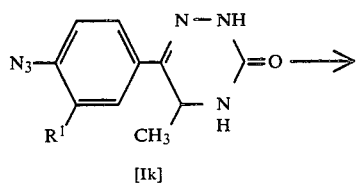
[Ik]
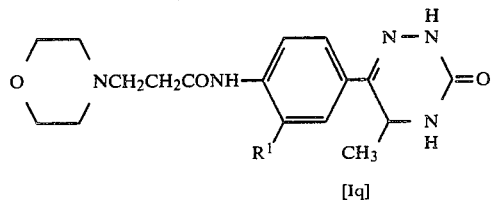
[Iq]
Process 13:
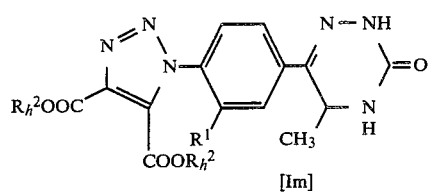
[Im]
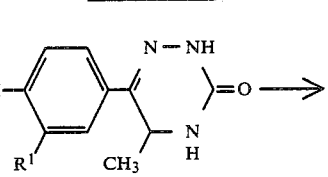
[Ir]
Process 10:
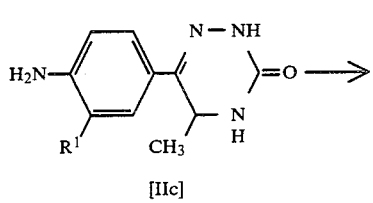
[IIc]
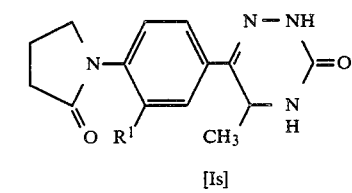
[Is]
Process 14:
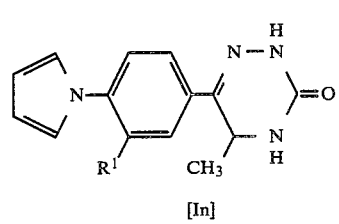
[In]
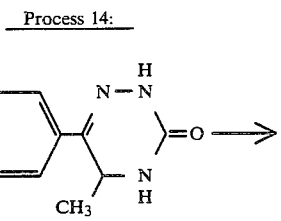
[It]
Process 11:
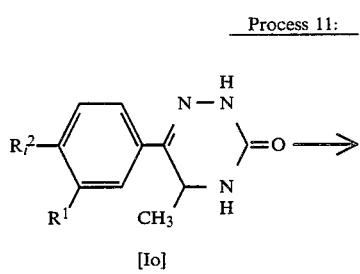
[Io]
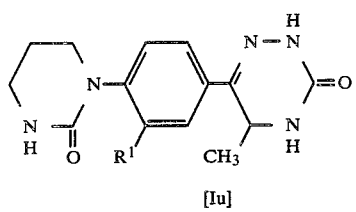
[Iu]
Process 15:
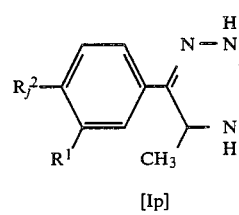
[Ip]
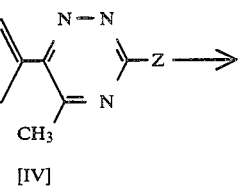
[IV]
Process 12:
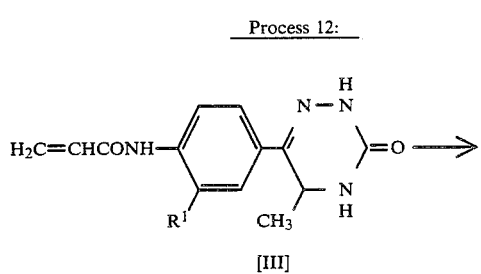
[III]
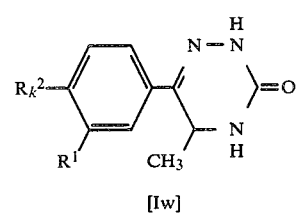
[Iw]
Process 16:

[Structure V: N-methyl-tetrahydroquinolinone fused with triazinone-CH₃-NH group] [V]

[Structure Ix: R_m²- and R_a¹-substituted phenyl with N—NH triazinone, CH₃, NH] [Ix]

Process 17:

[Structure If: H₂NHN— substituted phenyl with R¹, N—NH triazinone, CH₃, NH] [If]

[Structure Iy: N₃— substituted phenyl with R¹, N—N triazinone with H, CH₃, NH] [Iy]

Process 18:

[Structure Ic: R_e²—CH=N— substituted phenyl with R¹, N—NH triazinone, CH₃, NH] [Ic]

[Structure Iz: R_e²—CH₂NH— substituted phenyl with R¹, N—N triazinone with H, CH₃, NH] [Iz]

Process 19:

[Structure Iza: R_n²- and R¹-substituted phenyl with N—NH triazinone, CH₃, NH] [Iza]

[Structure Izb: R_p²- and R¹-substituted phenyl with N—N triazinone with H, CH₃, NH] [Izb]

Process 20:

[Structure Izc: R_q²- and R¹-substituted phenyl with N—NH triazinone, CH₃, NH] [Izc]

[Structure Izd: R_r²- and R¹-substituted phenyl with N—NH triazinone, CH₃, NH] [Izd]

wherein
$R^1$ and $R^2$ are the same as defined above;
$R_a^1$ is hydrazinocarbonyl(lower)alkyl;
$R_a^2$ is amino, lower alkylamino or ar(lower)alkylamino;
$R_b^2$ is N-methyl(lower)alkanoylamino or a group of the formula $$-\underset{\underset{R^3}{|}}{N}-CO-R^4$$

in which $R^3$ and $R^4$ are each as defined above;
$R_c^2$ is amino or hydroxy;
$R_d^2$ is mono- or di-(lower)alkylamino;
  mono- or di-(lower)alkynylamino;
  pyridylamino;
  mono- or di-(lower)alkylamino substituted by carboxy, hydroxy, lower alkoxy, lower alkoxycarbonyl, lower alkoxy(lower)alkoxy, aryl, furyl, pyridyl, phthalimido, succinimido;
  1-pyrrolidinyl;
  morpholino; or
  lower alkoxy substituted by hydroxy and lower alkylamino;
$R_e^2$ is furyl, pyridyl or aryl;
$R_f^2$ is mono- or di-(lower)alkylamino substituted by amino, carboxy, hydroxy or ureido;
  lower alkoxy substituted by hydroxy; or a group of the formula $$-\underset{\underset{R^3}{|}}{N}-CO-R_a^4$$

in which $R^3$ is as defined above; and
$R_a^4$ is α-hydroxybenzyl; carboxy; or lower alkyl substituted by amino, hydroxy, carboxy or piperazinyl being substituted with hydroxy(lower)alkyl, provided that at least one of the amino, hydroxy, carboxy and ureido groups is protected;

$R_g^2$ is the same as $R_f^2$, provided that one of the amino, hydroxy, carboxy and ureido groups is free or salt thereof;

$R_h^2$ is lower alkyl;

$R_i^2$ is a group of the formula

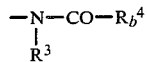

in which $R^3$ is as defined above; and
$R_b^4$ is lower alkyl substituted by halogen;

$R_j^2$ is a group of the formula

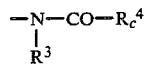

in which $R^3$ is as defined above; and
$R_c^4$ is lower alkyl substituted by morpholino, mono- or di-(lower)alkylamino, piperazinyl being substituted with hydroxy(lower)alkyl or furoyl, or pyrrolidino;

$R_k^2$ is mono- or di-(lower)alkylamino;
mono- or di-(lower)alkynylamino;
pyridylamino;
mono- or di-(lower)alkylamino substituted by amino, carboxy, hydroxy, ureido, lower alkoxy, lower alkoxy(lower)alkoxy, aryl furyl or pyridyl;
N-methyl(lower)alkanoylamino;
N-containing, 5- or 6-membered heterocyclic group optionally substituted by oxo or lower alkyl;
lower alkoxy substituted by hydroxy and lower alkylamino; or
a group of the formula

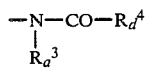

in which $R_a^3$ is hydrogen or lower alkyl; and
$R_d^4$ is pyridyl; aryl; styryl; alkynyl; α-hydroxybenzyl; carboxy; or lower alkyl substituted by halogen, amino, hydroxy, carboxy, morpholino, lower alkoxycarbonylamino, 1-methyl-2-oxo-1,2,3,4-tetrahydroquinolyloxy, mono- or di-(lower)alkylamino, piperazinyl being substituted with hydroxy(lower)alkyl or furoyl, or pyrrolidino;

$R_m^2$ is lower alkylamino;
$R_n^2$ is lower alkylamino substituted by amino;
$R_p^2$ is lower alkylamino substituted by ureido;
$R_q^2$ is mono- or di-(lower)alkylamino substituted by phthalimido or succinimido;
$R_r^2$ is mono or di(lower)alkylamino;
X is halogen;
Y is carbonyl or a formula

and Z is a leaving group.

Suitable "leaving group" is lower alkylthio optionally substituted with carboxy such as methylthio, ethylthio, butylthio, carboxymethylthio, 2-carboxyethylthio, 1-carboxyethylthio, 3-carboxypropylthio, 4-carboxybutylthio and the like.

The other definitions of each symbol are exemplified the ones as described hereinbefore.

PROCESS 1

The compound [Ia] and its salt can be prepared by reacting a compound [IIa] or its salt with a corresponding acylating agent in a conventional way.

The acylating agent may preferably be used in a form of acid or its reactive derivative, which may be exemplified an acid halide such as acid chloride, acid bromide, and the like, an acid anhydride such as a mixed acid anhydride with an acid (e.g., phosphoric acid, dialkylphosphorous acid, sulfurous acid, sulfuric acid, alkyl carbonate, aliphatic carboxylic acid, aromatic carboxylic acid, etc.), an activated acid amide with a heterocyclic compound (e.g., imidazole, triazole, etc.), an activated ester (e.g. cyanomethyl ester, 2,4-dinitrophenylester, etc.) and the like.

The acylation is preferably carried out in the presence of a base in a solvent under cooling or heating according to a conventional way.

Suitable base may include an amine (e.g., triethylamine, pyridine, N,N-dimethylaniline, etc.), an alkali metal hydroxide (e.g. sodium hydroxide, potassium hydroxide, etc.), an alkali metal carbonate (e.g., sodium carbonate, potassium carbonate, etc.), alkali metal bicarbonate (e.g. sodium bicarbonate, etc.), a salt of an organic acid (e.g., sodium acetate, etc.) and the like. In case that the base is liquid, the base can be used as a solvent.

Suitable solvent may include acetonitrile, benzene, chloroform, tetrahydrofuran, ethyl acetate, N,N-dimethylformamide (DMF) or any other solvent or an optional mixture thereof which does not adversely influence the reaction.

Further, when the acylating agent is used in a form of the free acid or its salt in this reaction, the reaction is preferably carried out in the presence of a conventional condencing agent such as a carbodiimide compound, a ketenimine compound, a phosphorous compound and the like.

PROCESS 2

The compound [Ib] and its salt can be prepared by reacting a compound [IIb] or its salt with a corresponding alkylating reagent in a conventional way.

Suitable alkylating agent may be lower alkyl halide such as alkyl chloride (e.g., propylchloride, butylchloride, etc.), alkyl bromide (e.g., methylbromide, ethylbromide, propylbromide, butylbromide, etc.), alkyl iodide (e.g., methyliodide, ethyliodide, propyliodide, etc.); alkylsulfate (e.g., dimethylsulfate, diethylsulfate, etc.), alkanesulfonate such as alkyl mesylate (e.g., methyl mesylate, ethyl mesylate, etc.), alkyl tosylate (e.g., methyl tosylate, ethyl tosylate, etc.), a combination of aldehyde or ketone compound and a reducing agent, and the like. The lower alkyl moiety in the above alkylating agent may be substituted and these alkylating agents can be reacted in a similar manner.

Pyridyl compounds are also obtained by using pyridyl chloride instead of the above alkyl halide.

This reaction can be conducted in the presence or absence of a suitable base as mentioned in Process 1 or potassium iodide, sodium iodide, and the like in a suitable solvent under warming or heating.

Preferred alkylating agent for methylation is a combination of formaldehyde and a reducing agent such as lithium borohydride, sodium borohydride, potassium borohydride, sodium cyanoborohydride or lithium hydride etc.

Suitable solvent may include water, alcohol (e.g. methanol, ethanol, propanol etc.), aromatic solvent (e.g. benzene, toluene, xylene etc.), acetonitrile, chloroform, DMF, ethyl acetate and the like.

PROCESS 3

The compound [Ic] and its salt can be prepared by reacting a compound [IIc] or its salt with a compound of the formula [VII].

This reaction can be conducted in a conventional solvent such as benzene, toluene, DMF and the like which does not adversely influence the reaction.

The reaction temperature is not critical and the reaction is usually carried out under warming or heating.

The reaction can optionally be conducted in the presence of metal salt (e.g. zinc chloride) and the like.

PROCESS 4

The compound [Ie] and its salt can be prepared by subjecting the compound [Id] or its salt to an elimination reaction of the protective group.

Suitable "protective group" for hydroxy may include acyl such as lower alkanoyl (e.g. formyl, acetyl, propionyl, etc.), ar(lower)alkyl such as benzyl and 4-nitrobenzyl and the like.

Suitable "protective group" for amino and ureido group may include acyl as stated above, lower alkoxycarbonyl (e.g. benzyloxycarbonyl, tert-butoxycarbonyl, trichloroethoxycarbonyl, etc.), trityl, phthalimido, succinimido and the like.

Suitable "protective group" for carboxy may include ester such as lower alkyl ester (e.g. methyl ester, ethyl ester, tert-butyl ester etc.), substituted lower alkyl ester (e.g. trichloroethyl ester, methoxymethyl ester etc.), benzyl ester (e.g. p-methoxybenzyl ester, p-nitrobenzyl ester etc.) and the like.

The elimination reaction of the protective group can be conducted in a conventional way such as solvolysis (e.g. hydrolysis, aminolysis, alcoholysis, etc.), hydrogenolysis, or the like according to a kind of the protective group.

Among these methods, in case of the protective group is an acyl group such as a lower alkanoyl and lower alkoxycarbonyl, or ester group, solvolysis in the presence of a base or an acid is one of the common and preferable methods.

Suitable base may be the one as mentioned in Process 1.

Suitable acid may include an organic or inorganic acid such as hydrochloric acid, boron trihalide, formic acid, acetic acid, sulfuric acid, trifluoroacetic acid, p-toluenesulfonic acid and the like.

Further, aminolysis by using hydrazine or ammonia is preferable, too.

The solvolysis can be carried out in a solvent such as water, alcohol, dichloromethane, and the like, or without a solvent. The reaction temperature is not critical and the reaction can be carried out under cooling, warming or heating.

PROCESS 5

The compound [If] and its salt can be prepared by reacting a compound [IIc] or its salt with nitrous acid or its salt (e.g. sodium nitrite, etc.) and then by reducing the intermediate. The intermidiate obtained in the initial step is diazonium salt and the intermediate can optionally be isolated and purified, but it can be used in the second step without isolation.

The diazonium salt can be prepared in a conventional way, for example, compound [IIc] and nitrous acid are stirred in a solvent such as water, alcohol in the presence of a mineral acid (e.g. hydrochloric acid, hydrobromic acid, sulfuric acid, etc.). The reaction temperature is not critical but usually carried out under cooling or ambient temperature.

The reduction of the diazonium salt can be conducted in a conventional way for example, by using sodium sulfite or stannus chloride in the presence of a mineral acid. The reaction temperature and solvent is not critical but usually be conducted in a similar manner to the initial step.

PROCESS 6

The compound [Ig] and its salt can be prepared by reacting a compound [IIc] or its salt with nitrous acid or its salt (e.g. sodium nitrite, etc.) and then reacting with sulfur dioxide in the presence of cupric chloride.

The initial step to form a diazonium salt can be conducted in a similar manner to that of Process 5.

The reaction of the diazonium salt with sulfur dioxide in the presence of cupric chloride can be conducted in a suitable solvent such as water, alcohol and the like. The reaction preferably be conducted in the presence of an acid such as formic acid, acetic acid and the like. The reaction temperature is not critical but preferably be conducted under cooling or warming.

PROCESS 7

The compound [Ih] and its salt can be prepared by reacting a compound [If] or its salt with methyl acetoacetate or acetyl acetone.

This reaction can be conducted in solvent such as water, alcohol, aromatic solvent, chloroform and the like under warming or heating.

This reaction optionally be conducted in the presence or absence of an acid as exemplified in Process 4.

PROCESS 8

The compound [Ij] and its salt can be prepared by reacting a compound [Ii] or its salt with sodium azide in a solvent.

This reaction preferably be conducted in the presence of sodium acetate or a base as exemplified in Process 1.

This reaction can be conducted in a solvent as exemplified in Process 1 under warming or heating.

PROCESS 9

The compound [Im] and its salt can be prepared by reacting a compound [Ik] or its salt with di(lower alkyl)acetylenedicarboxylate.

This reaction preferably be conducted in a solvent as exemplified in Process 1 under warming or heating.

PROCESS 10

The compound [In] and its salt can be prepared by reacting a compound [IIc] or its salt with 2,5-di(lower)alkoxytetrahydrofuran.

This reaction can be conducted in the presence or absence of an organic or inorganic acid as exemplified in Process 4. The reaction can be conducted in a solvent such as water, alcohol, aromatic solvent and the like under warming or heating. The reaction preferably be conducted in the presence of an acid as exemplified in Process 4.

PROCESS 11

The compound [Ip] and its salt can be prepared by reacting a compound [Io] or its salt with a compound of the formula $R_e^4$; or its salt (wherein $R_e^4$ is morpholine, mono- or di-(lower)alkylamine, piperazine being substituted with hydroxy(lower)alkyl or furoyl, or pyrrolidine) or its salt.

The reaction can be conducted in a similar manner to that of Process 2.

PROCESS 12

The compound [Iq] and its salt can be prepared by reacting a compound [III] or its salt with morpholine under warming or heating.

This reaction can be conducted in the presence or absence of alkali metal hydroxide (e.g. sodium hydroxide, potassium hydroxide, etc.), alkaline earth metal hydroxide (e.g. calcium hydroxide, etc.).

This reaction can optionally be conducted in a solvent as exemplified in Process 1.

PROCESS 13

The compound [Is] and its salt can be prepared by treating a compound [Ir] or its salt with sodium hydride in a solvent as exemplified in Process 1.

The reaction temperature is not critical but preferably be conducted under cooling or warming.

PROCESS 14

The compound [Iu] and its salt can be prepared by heating the compound [It] or its salt.

The heating is conducted over 100° C.

This reaction can optionally be conducted in the presence of a base as exemplified in Process 1.

PROCESS 15

The compound [Iw] and its salt can be prepared by treating a compound [IV] or its salt with a base and then reducing the reaction product.

Suitable base to be used in the first step may include alkali metal hydroxide (e.g. sodium hydroxide, potassium hydroxide, etc.), alkaline earth metal hydroxide (e.g. calcium hydroxide, etc.), and the like.

The treatment of the compound [IV] or its salt with a base can be preferably conducted in a polar solvent such as alcohol (e.g., methanol, ethanol, propanol, etc.), water, ether (e.g., dimethyl ether, diethyl ether, tetrahydrofuran, dioxane, etc.), aromatic solvent (e.g., benzene, toluene, xylene, etc.).

The reaction product obtained in the initial step is the compound of the following formula [VI] or its salt.

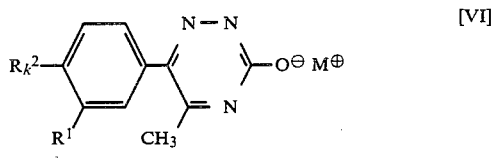

(wherein $R^1$ and $R_k^2$ are each as defined above, and M is an alkali metal or alkaline earth metal ion)

Said compound [VI] and its salt can be optionally isolated and purified, but they can be used in the second step without isolation or purification, also.

The reduction of the compound [VI] or its salt in the second step can be carried out in a conventional method, for example, by using a reducing agent such as lithium borohydride, sodium borohydride, potassium borohydride, sodium cyanoborohydride or lithium aluminum hydride etc.; by chemical reduction using metal (e.g., zinc, iron, copper, etc.) and acid (e.g., hydrochloric acid, sulfuric acid, etc.), or metal (e.g., sodium, lithium, zinc, etc.) and base (e.g. ammonia, sodium hydroxide, etc.); or by catalytic reduction. The catalytic reduction is usually carried out in the presence of a conventional catalyst, such as Raney nickel, palladium, platinum, rhodium, copper, etc. preferably at ambient temperature under atmospheric pressure and in a conventional solvent. The reduction using a reducing agent is usually carried out in a conventional solvent, preferably a polar solvent, such as water, alcohol, acetonitrile, DMF, DMSO, and the like.

The present reaction can be conducted under cooling or slightly elevated temperature, and optionally in the presence of a base such as sodium hydroxide, sodium carbonate, potassium carbonate, etc.

PROCESS 16

The compound [Ix] and its salt can be prepared by treating the compound [V] with hydrazine under warming or heating.

This reaction can be conducted in the presence or absence of a solvent such as aromatic solvent, DMF and the like.

PROCESS 17

The compound [Iy] and its salt can be prepared by reacting a compound [If] or its salt with nitrous acid or its salt (e.g. sodium nitrite) under cooling or warming.

The reaction can be conducted according to a similar manner to that of Process 5.

PROCESS 18

The compound [Iz] and its salt can be prepared by reducing the compound [Ic] or its salt.

The reduction can be conducted according to a similar manner to the latter part of Process 15.

PROCESS 19

The compound [Izb] and its salt can be prepared by reacting a compound [Iza] or its salt with alkali metal cyanate.

Suitable "alkali metal cyanate" may include potassium cyanate, sodium cyanate and the like.

The reaction can be conducted in a solvent such as water, alcohol in the presence of an acid such as formic acid, acetic acid and the like.

The reaction temperature is not critical but preferably be conducted at ambient temperature or warming.

PROCESS 20

The compound [Izd] and its salt can be prepared by reducing the compound [Izc] or its salt.

The reduction can be conducted according to a similar manner to the latter part of Process 15.

The above reaction conditions such as temperature, solvent, kinds of acid and base, etc. in Process 1 to 20 are cited preferable ones, and the modifications of them by persons who skilled in the art are included in this invention.

Suitable salt of the starting compounds to be used in the above processes may be the same as those of the compound [I].

The starting compounds of the above processes contain new and known compounds, and the new compounds can be prepared by the methods described below in Preparations or the methods chemically equivalent thereto.

The object compounds [I] obtained in the above Process 1 to 20 can be isolated and purified in a conventional manner, for example, extraction, precipitation, fractional chromatography, fractional crystallization, recrystallization, and the like.

The object compounds [I] thus prepared can be transformed into a pharmaceutically acceptable salt by a conventional method, if desired.

In case that the object compound [I] is a mixture of the optical isomers, optical resolution can optionally be conducted by conventional method.

The following antihypertensive test data, inhibitory activity test data on platelet aggregation and antiulcer test data show that the compound [I] of the present invention exhibit antihypertensive activity, inhibitory activity on platelet aggregation and antiulcer activity, and are useful as antihypertensive agents for treating hypertension and as antithrombotic agents for treating thrombosis and also as antiulcer drugs for treating ulcer in animals and human beings.

TEST METHOD A

Five-week old male Wister rats were uninephrectomized under anesthesia. Deoxycorticosterone acetate (DOCA) (30 mg/kg), suspended in peanut oil, was injected subcutaneously twice a week and 1% saline was substituted for the drinking water. Animals with mean blood pressure 150–200 mmHg were used for experiment between 5 and 7 weeks after surgery.

The test compounds were administered orally. Blood pressure was measured at the femoral artery by means of a pressure transducer and recorded as electrically integrated values of mean arterial pressure.

TEST RESULTS A

Mean ratios of maximum decrease of blood pressure (mmHg) were shown in the following table.

| Test Compound (Example No.) | Dose | Effect Max (%) |
|---|---|---|
| 5-(7) | a | 18.7 |
| 5-(7) | b | 51.8 |
| 13-(3) | a | 22 |
| 13-(3) | b | 50 |
| 29 | a | 11.1 |
| 29 | b | 47.5 |

*a: The test compound were administered orally in dose of 0.1 mg/kg.
*b: The test compound were administered orally in a dose of 1 mg/kg.

Furthermore, the above mentioned antihypertensive activity of these compounds were observed to continue more than 6 hours.

TEST METHOD B

Platelet rich plasma (PRP) which contains $6.5$–$7.5 \times 10^8$ platelet/ml was prepared from rabbit blood. To the 200 μl of PRP, 5 μl of calcium chloride (1 mM) and 50 μl of pH 7.4 Tris-acetate solution (5 mM) containing 120 mM NaCl and test compound were added successively, and then stirred for 2 min. at 37° C. To the solution, 5 μl of adenosine diphosphate (ADP) (2.5 μM) or collagen (2.5 μg/ml) was added as an aggregation inducer. Aggregation was measured by using an aggregometer (NKK HEMA TRACER 1). $ID_{50}$ was shown in Table 2.

| | Test results B | |
|---|---|---|
| | $ID_{50}$ (Mol) | |
| Test Compound | ADP | Collagen |
| 5-(19) | $1.1 \times 10^{-7}$ | $5.3 \times 10^{-9}$ |
| 13-(3) | $3.2 \times 10^{-7}$ | $1.5 \times 10^{-7}$ |
| 21-(1) | $1.9 \times 10^{-7}$ | $4.7 \times 10^{-8}$ |
| 22-(1) | $6.8 \times 10^{-8}$ | $1.6 \times 10^{-8}$ |

TEST METHODS C

Five male Sprague-Dowley rats, aged 7 weeks and weighing about 200 g, were used per group for the study on ethanol ulcer after the fast for 24 hours.

Test compound was suspended in 0.1% methylcellulose aqueous solution, and the suspension (5 ml/kg) was orally given to each rat.

The control group was given a vehicle, i.e. 0.1% methylcellulose aqueous solution (5 ml/kg), alone in the same way.

Absolute ethanol (5 ml/kg) was orally administered 30 minutes after dosing with test compound, and one hour later, the rats were sacrificed and their stomachs were removed. The area of ulcers of each rat was measured. The mean area (mm$^2$) in the medicated group was compared with that in the control group.

| | Test result C | |
|---|---|---|
| Test Compound (Example No.) | Dose | Effect Max (%) |
| 13-(4) | c | 67.0 |

*c: The test compound was administered orally in dose of 32 mg/kg.

As being apparent from the above test results, the object compounds [I] of the present invention are useful for antihypertensive medicines, antithrombotic medicines and antiulcer medicines.

The effective ingredient may usually be administered with a dose of 0.01 mg/kg to 500 mg/kg, 1 to 4 times a day in preparations such as tablet, granule, powder, capsule, syrup, injection, suppository and the like. However, the above dosage may be increased or decreased according to the age, weight or conditions of the patient or the administering method.

The pharmaceutical preparation may be prepared in a conventional manner.

The following Preparations and Examples are given only for the purpose of illustrating the present invention in more detail.

PREPARATION 1

(1) 4'-Acetamido-2-hydroxyiminopropiophenone (1.87 g) was added to a suspension of thiosemicarbazide (1 g) and acetic acid (0.1 ml) in a mixture of methanol (15 ml) and water (3 ml) and then heated at 100° for 39 hours with stirring. After cooling, the resultant precipitates were collected by filtration, washed with methanol, and then dried to give 1.7 g of 4'-acetamido-2-hydroxyiminopropiophenone thiosemicarbazone.

NMR (DMSO-d$_6$, δ): 2.08 (3H, s), 2.17 (3H, s), 7.18 (2H, d, J=8 Hz), 7.73 (2H, d, J=8 Hz), 8.13 (1H, b.s.), 8.63 (2H, b.s.), $$\left.\begin{array}{l}9.10\ (b.s.)\\10.23\ (b.s.)\end{array}\right\}\ (1H) \qquad \left.\begin{array}{l}11.69\ (s)\\12.26\ (s)\end{array}\right\}\ (1H)$$

(2) A mixture of the above object compound (34.74 g) of (1) and potassium carbonate (35.88 g) in water (300 ml) was refluxed for 3 hours under stirring. After cooling, sodium chloroacetate (20.6 g) was added to the solution at ambient temperature and stirring was continued for 2 hours. The aqueous solution was washed with chloroform, acidified with hydrochloric acid, and allowed to stand over night in a refrigerator. The precipitates were collected by filtration, washed with water and dried to give 6-(4-acetamidophenyl)-3-carboxymethylthio-5-methyl-1,2,4-triazine (16.7 g).

NMR (DMSO-d$_6$, δ): 2.10 (3H, s), Ca. 2.5 (3H, s), 3.96 (2H, s), 7.58 (2H, d, J=8 Hz), 7.77 (2H, d, J=8 Hz), 10.35 (1H, s)

(3) A mixture of the above obtained compound (10.61 g) of (2), 10% aqueous solution of potassium hydroxide (46 ml) and methanol (45 ml) was heated at 60° C. for 2 hours with stirring. To the solution was added portionwise sodium borohydride (1.64 g) with stirring under ice cooling. After stirring for 1 hour at room temperature, the mixture was treated with 10% hydrochloric acid to decompose excess sodium borohydride and concentrated to a small volume. The resultant precipitates were collected by filtration, washed with water and dried to give 6.12 g of 6-(4-acetamidophenyl)-5-methyl-4,5-dihydro-1,2,4-triazin-3(2H)-one.

mp: 272° to 273° C. (from 60% ethanol)

NMR (DMSO-d$_6$, δ): 1.22 (3H, d, J=7 Hz), 2.08 (3H, s), 4.64 (1H, m), 7.43 (1H, b.s.), 7.68 (4H, s), 9.96 (1H, d, J=2 Hz), 10.10 (1H, s)

Anal. Calcd. for C$_{12}$H$_{14}$N$_4$O$_2$.H$_2$O: C, 54.54; H, 6.10; N, 21.20; Found: C, 54.87; H, 6.00; N, 21.45

(4) A mixture of the above obtained compound (3.35 g) of (3) and 100% hydrazine hydrate (33 ml) was heated at 120° C. for 2 hours under stirring and allowed to stand overnight at room temperature. The precipitates were collected by filtration, washed with methanol, and dried. The filtrate was evaporated in vacuo and the residue was triturated in ethanol to give the second crop. The combined crude products were recrystallized from 60% aqueous ethanol to give 6-(4-aminophenyl)-5-methyl-4,5-dihydro-1,2,4-triazin-3(2H)-one (1.61 g), mp 248° to 249.5° C.

NMR (DMSO-d$_6$, δ): 1.16 (3H, d, J=7 Hz), 4.52 (1H; d, q; J=3.5, 7 Hz), 5.41 (2H, s), 6.58 (2H, d, J=8 Hz), 7.23 (1H, b.s.), 7.42 (2H, d, J=8 Hz), 9.67 (1H, d, J=2 Hz).

Anal. Calcd. for C$_{10}$H$_{12}$N$_4$O: C, 58.81; H, 5.92; N, 27.44; Found: C, 58.64; H, 5.96; N, 27.33

PREPARATION 2

N-Chlorosuccinimide (0.135 g) was added portionwise to a solution of the object compound (0.2 g) of preparation 1 in dimethylformamide (3 ml) and stirred for 1 hour under ice cooling. The solution was extracted with chloroform after an addition of water and the extract was dried over sodium sulfate and evaporated in vacuo.

The oily residue was triturated with chloroform to give 6-(4-amino-3-chlorophenyl)-4,5-dihydro-5-methyl-1,2,4-triazin-3(2H)-one (0.02 g), mp 229° to 231° C. (from methanol).

NMR (DMSO-d$_6$, δ): 1.16 (3H, d, J=6.6 Hz), 4.52 (1H, m), 5.64 (2H, s), 6.77 (1H, d, J=8 Hz), 7.25 (1H, b.s.), 7.38 (1H; d, d; J=2, 8 Hz), 7.53 (1H, d, J=2 Hz), 9.73 (1H, b.s.)

PREPARATION 3

N-Bromosuccinimide (4.36 g) was added portionwise to a solution of the object compound (5 g) of preparation 1 in DMF (70 ml) and the solution was stirred for 1 hour under ice cooling and then for 2 hours at room temperature. The solution was concentrated to a small column under reduced pressure and diluted with water. The resulting precipitates were collected by filtration, washed with water, and dried in a desiccator to give 6-(4-amino-3-bromophenyl)-4,5-dihydro-5-methyl-1,2,4-triazin-3(2H)-one (5.76 g), mp 222° to 224° C. (from ethanol).

NMR (DMSO-d$_6$, δ): 1.16 (3H, d, J=6.6 Hz), 4.53 (1H, m), 5.62 (2H, s), 6.77 (1H, d, J=8 Hz), 7.27 (1H, b.s.), 7.43 (1H; d,d; J=2, 8 Hz), 7.67 (1H, d, J=2 Hz), 9.76 (1H, b.s.)

EXAMPLE 1

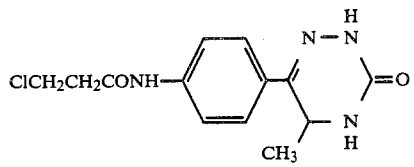

β-Chloropropionyl chloride (1.25 ml) was added dropwise to a stirred solution of 6-(4-aminophenyl)-5-methyl-4,5-dihydro-1,2,4-triazin-3(2H)-one (2.04 g) and triethylamine (1.53 ml) in N,N-dimethylformamide (DMF) (10.5 ml) under ice cooling and the stirring was continued for 30 minutes. The solution was evaporated in vacuo and the residue as triturated with water under ice-cooling. The precipitates were collected by filtration, washed with water and dried to give 6-[4-(β-chloropropionylamino)phenyl]-5-methyl-4,5-dihydro-1,2,4-triazin-3(2H)-one (1.55 g).

NMR (DMSO-d$_6$, δ): 1.22 (3H, d, J=7 Hz), 2.86 (2H, t, J=6 Hz), 3.91 (2H, t, J=6 Hz), 4.63 (1H; d, q; J=3.6, 7 Hz), 7.38 (1H, b.s.), 7.66 (4H, s), 9.94 (1H, b.s.), 10.18 (1H, b.s.)

EXAMPLE 2

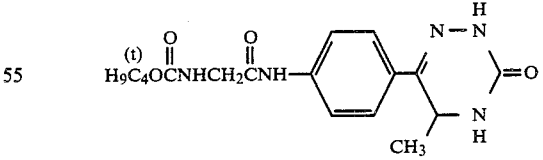

To a stirred solution of 6-(4-aminophenyl)-5-methyl-4,5-dihydro-1,2,4-triazin-3(2H)-one (2.28 g) in DMF (30 ml) was added dropwise a solution of mixed anhydride prepared from N-t-butoxycarbonylglycine (3.912 g), triethylamine (2.371 g) and ethyl chloroformate (2.425 g) in methylene chloride (15 ml) with stirring under ice-cooling. The stirring was continued for 1 hour at the same temperature. The mixture was filtered and the filtrate was evaporated in vacuo. The residue was dissolved in ethyl acetate, washed successively with water, an aqueous solution of sodium bicarbonate and water, dried and evaporated in vacuo. The residue was dissolved in methanol (12 ml) and conc. ammonia (1.5 ml) was added thereto. After stirring for 2 hours at room temperature, the resulting precipitates were collected by filtration, washed with methanol, and dried to give 6-[4-[N-(t-butoxycarbonyl)glycylamino]phenyl]-5-methyl-4,5-dihydro-1,2,4-triazin-3(2H)-one (1.74 g).

NMR (DMSO-$d_6$, δ): 1.22 (3H, d, J=6.2 Hz), 1.40 (9H, s), 3.76 (2H, d, J=5.8 Hz), 4.62 (1H; d, q; J=2.8, 6.2 Hz), 6.96 (1H, b.s.), 7.36 (1H, b.s.), 7.65 (4H, s), 9.90 (1H, b.s.), 10.00 (1H, b.s.)

EXAMPLE 3

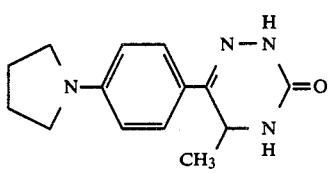

A mixture of 6-(4-aminophenyl)-5-methyl-4,5-dihydro-1,2,4-triazin-3(2H)-one (2.04 g), 1,4-dibromobutane (2.59 g), potassium carbonate (0.35 g) and potassium iodide (0.5 g) in DMF (10 ml) was heated at 80° C. for 5 hours under stirring, and then evaporated in vacuo. After addition of 30% aqueous methanol to the residue, the resulting precipitates were collected by filtration and recrystallized from a mixture of methanol and chloroform (7:3) to give 6-(4-pyrrolidinophenyl)-5-methyl-4,5-dihydro-1,2,4-triazin-3(2H)-one (0.65 g).

mp: 276° to 281° C.

NMR (DMSO-$d_6$, δ): 1.17 (3H, d, J=7 Hz), 1.8–2.1 (4H, m), Ca. 3.1–3.4 (4H, m), 4.53 (1H; d, q; J=3, 7 Hz), 6.53 (2H, d, J=8 Hz), 7.22 (1H, b.s.), 7.47 (2H, d, J=8 Hz), 9.58 (1H, b.s.)

Anal. Calcd. for $C_{14}H_{18}N_4O$: C, 65.09; H, 7.02; N, 21.69; Found: C, 64.92; H, 6.97; N, 21.65

EXAMPLE 4

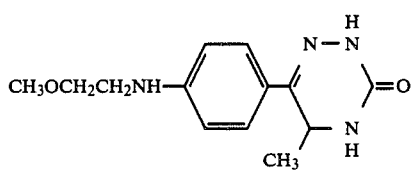

A mixture of 6-(4-aminophenyl)-5-methyl-4,5-dihydro-1,2,4-triazin-3(2H)-one (2 g), 2-methoxyethyl-p-toluenesulfonate (3.8 g), potassium iodide (0.5 g) and potassium carbonate (1.3 g) in DMF (18 ml) was heated at 80° C. for 16 hours and evaporated in vacuo. The residue was extracted with ethyl acetate after an addition of water and the extract was washed with water, dried over magnesium sulfate, and evaporated in vacuo. The oily residue was triturated with ethyl acetate, collected by filtration, and recrystallized from aqueous ethanol to give 6-[4-(2-methoxyethylamino)phenyl]-5-methyl-4,5-dihydro-1,2,4-triazin-3(2H)-one (0.41 g).

mp: 160° to 165° C.

NMR (DMSO-$d_6$, δ): 1.17 (3H, d, J=6.8 Hz), 3.1–3.7 (7H, m), 4.50 (1H; d, q; 3.6, 6.8 Hz), 6.59 (2H, d, J=9 Hz), 7.20 (1H, b.s.), 7.45 (2H, d, J=9 Hz), 9.64 (1H, b.s.)

EXAMPLE 5

The following compounds were obtained from 6-(4-aminophenyl)-5-methyl-4,5-dihydro-1,2,4-triazin-3(2H)-one or its derivatives at the amino or benzene ring according to a similar manner to that of Example 1 or 2.

EXAMPLE 5-(1)

6-[4-(D-2-Acetoxypropionamido)phenyl]-5-methyl-4,5-dihydro-1,2,4-triazin-3(2H)-one NMR (DMSO-$d_6$, δ): 1.22 (3H, d, J=6.5 Hz), 1.44 (3H, d, J=7 Hz), 2.11 (3H, s), 4.65 (1H; d, q; J=3.5, 6.5 Hz), 5.08 (1H, q, J=7 Hz), 7.30–7.50 (1H, m), 7.67 (4H, s), 9.90–10.05 (1H, m), 10.16 (1H, s)

EXAMPLE 5-(2)

6-(4-Acetoxyacetamido-3-bromophenyl)-5-methyl-4,5-dihydro-1,2,4-triazin-3(2H)-one IR (Nujol): 3390, 3200, 3140 (shoulder), 3090, 1760, 1715, 1690 $cm^{-1}$ NMR (DMSO-$d_6$, δ): 1.21 (3H, d, J=7 Hz), 2.14 (3H, s), 4.4–4.9 (1H, m), 4.73 (2H, s), 7.48 (1H, b.s.), 7.73 (2H, s), 8.00 (1H, s), 9.56 (1H, s), 10.08 (1H, d, J=1.8 Hz)

EXAMPLE 5-(3)

6-(3-Chloro-4-pyruvoylaminophenyl)-5-methyl-4,5-dihydro-1,2,4-triazin-3(2H)-one mp: 283° to 287° C. (dec.) (recrystallized from aqueous DMF)

IR (Nujol): 3340, 3210, 3090, 1710, 1700 (shoulder), 1690 $cm^{-1}$

NMR (DMSO-$d_6$, δ): 1.21 (3H, d, J=6.4 Hz), Ca. 2.4–2.7 (3H, s), 4.69 (1H; d, q; J=3.2, 6.4 Hz), 7.50 (1H, b.s.), 7.72 (1H; d, d; J=2.2, 8.6 Hz), 7.87 (1H, d, J=2.2 Hz), 8.08 (1H, d, J=8.6 Hz), 9.76 (1H, b.s.), 10.11 (1H, d, J=2 Hz)

Anal. Calcd. for $C_{13}H_{13}ClN_4O_3$: C, 50.58; H, 4.24; N, 18.15; Found: C, 50.38; H, 4.24; N, 18.47

EXAMPLE 5-(4)

6-[4-(3-Acetoxypropionamido)phenyl[-5-methyl-4,5-dihydro-1,2,4-triazin-3(2H)-one NMR (DMSO-$d_6$, δ): 1.19 (3H, d, J=6.5 Hz), 1.97 (3H, s), 2.43–2.92 (2H), 4.29 (2H, t, J=6 Hz), 4.61 (1H; d, q; J=2.5, 6.5 Hz), 7.27–7.47 (1H, m), 7.67 (4H, s), 9.93 (1H, m), 10.13 (1H, m)

EXAMPLE 5-(5)

6-(4-Acetoxyacetylaminophenyl)-5-methyl-4,5-dihydro-1,2,4-triazin-3(2H)-one mp: 234.5° to 236° C. (recrystallized from 50% aqueous ethanol)

NMR (DMSO-$d_6$, δ): 1.21 (3H, d, J=7 Hz), 2.13 (3H, s), 4.4–4.8 (1H, complex), 4.66 (2H, s), 7.38 (1H, b.s.), 7.64 (4H, s), 9.92 (1H, b.s.), 10.15 (1H, b.s.)

EXAMPLE 5-(6)

6-(4-Nicotinamidophenyl)-5-methyl-4,5-dihydro-1,2,4-triazin-3(2H)-one mp: 288° to 290° C. (recrystallized from aqueous DMF)

IR (Nujol): 3350, 3200, 3080, 1700, 1655 $cm^{-1}$

NMR (DMSO-$d_6$, δ): 1.22 (3H, d, J=7 Hz), 4.64 (1H; d, q; J=3, 7 Hz), 7.43 (1H, b.s.), Ca. 7.5–7.7 (1H, m), 7.77 (4H, s), 8.28 (1H; t, d; J=2, 8 Hz), 8.73 (1H; d, d;

J=2, 5 Hz), 9.10 (1H, d, J=2 Hz), 9.92 (1H, b.s.), 10.50 (1H, s)

Anal. Calcd. for $C_{16}H_{15}N_5O_2$: C, 62.13; H, 4.89; N, 22.64; Found: C, 62.22; H, 4.97; N, 22.66

EXAMPLE 5-(7)

6-[4-(2-Chloropropionylamino)phenyl]-5-methyl-4,5-dihydro-1,2,4-triazin-3(2H)-one mp: 213° to 215° C. (recrystallized from 80% aqueous ethanol)

NMR (DMSO-d$_6$, δ): 1.22 (3H, d, J=7 Hz), 1.64 (3H, d, J=7 Hz), Ca. 4.4–4.8 (1H, m), 4.66 (1H, q, J=7 Hz), 7.41 (1H, b.s.), 7.73 (4H, s), 9.92 (1H, b.s.), 10.40 (1H, b.s.)

Anal. Calcd. for $C_{13}H_{15}ClN_4O_2$: C, 52.97; H, 5.13; N, 19.01; Found: C, 52.71; H, 5.28; N, 18.85

(EXAMPLE 5-(8)

6-[4-(3-Ethoxycarbonylpropionylamino)phenyl]-5-methyl-4,5-dihydro-1,2,4-triazin-3(2H)-one mp: 216° to 219° C. (recrystallized from 70% aqueous ethanol)

IR (Nujol): 3250, 1725, 1670 cm$^{-1}$

NMR (DMSO-d$_6$, δ): 1.0–1.4 (6H, m), 2.59 (4H, s), 4.03 (2H, q, J=7 Hz), 4.58 (1H; d, q; J=3.8, 7 Hz), 7.29 (1H, b.s.), 7.55 (4H, s), 9.82 (1H, b.s.), 9.98 (1H, b.s.)

EXAMPLE 5-(9)

6-[4-(4-Chlorobutyrylamino)phenyl]-5-methyl-4,5-dihydro-1,2,4-triazin-3(2H)-one

NMR (DMSO-d$_6$, δ): 1.22 (3H, t, J=7 Hz), 1.79–2.36 (2H, m), 2.36–2.73 (2H, complex), 3.71 (2H, t, J=6 Hz), 4.62 (1H; d, q; J=3, 7 Hz), 7.36 (1H, b.s.), 7.66 (4H, s), 9.89 (1H, b.s.), 10.07 (1H, s)

EXAMPLE 5-(10)

6-(4-Ethoxalylaminophenyl)-5-methyl-4,5-dihydro-1,2,4-triazin-3(2H)-one mp: 244° to 247° C. (dec.) (recrystallized from 70% aqueous ethanol)

IR (Nujol): 3380, 3200, 3080, 1700 (broad) cm$^{-1}$

NMR (DMSO-d$_6$, δ): 1.22 (3H, d, J=6.6 Hz), 1.33 (3H, t, J=7.2 Hz), 4.33 (2H, q, J=7.2 Hz), 4.65 (1H; d, q; J=3.4, 6.6 Hz), 7.41 (1H, b.s.), 7.69 (2H, d, J=10 Hz), 7.86 (2H, d, J=10 Hz), 9.97 (1H, d, J=1.4 Hz), 10.86 (1H, s)

Anal. Calcd. for $C_{14}H_{16}N_4O_4$: C, 55.26; H, 5.30; N, 18.41; Found: C, 54.98; H, 5.34; N, 18.44

EXAMPLE 5-(11)

6-[4-(N-Methyl-N-benzoylamino)phenyl]-5-methyl-4,5-dihydro-1,2,4-triazin-3(2H)-one mp: 135° to 138° C.

NMR (DMSO-d$_6$, δ): 1.14 (3H, d, J=7 Hz), 3.38 (3H, s), Ca. 4.5–4.7 (1H, m), Ca. 7.2 (2H, d, J=8 Hz), 7.26 (5H, s), Ca. 7.4 (1H, b.s.), 7.63 (2H, d, J=8 Hz), 9.96 (1H, d, J=1.4 Hz)

EXAMPLE 5-(12)

6-[4-(N-Methyl-N-cinnamoylamino)phenyl]-5-methyl-4,5-dihydro-1,2,4-triazin-3(2H)-one mp: 125° to 128° C. (dec.)

NMR (DMSO-d$_6$, δ): 1.26 (3H, d, J=7 Hz), 3.35 (3H, s), 4.70 (1H; d, q; J=3, 7 Hz), 6.50 (1H, d, J=15.5 Hz), 7.37 (2H, d, J=8.6 Hz), 7.38 (5H, s), Ca. 7.3–7.6 (1H, b.s.), Ca. 7.6 (1H, d, J=15.5 Hz), 7.85 (2H, d, J=8.6 Hz), 10.13 (1H, b.s.)

EXAMPLE 5-(13)

6-[4-[N-Benzyl-N-(β-chloropropionyl)amino]phenyl]-5-methyl-4,5-dihydro-1,2,4-triazin-3(2H)-one NMR (DMSO-d$_6$, δ): 1.21 (3H, d, J=7 Hz), 2.64 (2H, t, J=6 Hz), 3.83 (2H, t, J=6 Hz), 4.64 (1H; d, q; J=3.4, 7 Hz), 4.94 (2H, s), 7.24 (2H, d, J=9 Hz), Ca. 7.1 to 7.4 (5H, m), 7.46 (1H, b.s.), 7.75 (2H, d, J=9 Hz), 10.10 (1H, b.s.)

EXAMPLE 5-(14)

6-(4-Propioloylaminophenyl)-5-methyl-4,5-dihydro-1,2,4-triazin-3(2H)-one mp: 243° C. (dec.)

NMR (DMSO-d$_6$, δ): 1.20 (3H, d, J=6.5 Hz), 4.43 (1H, s), 4.64 (1H; d, q; J=3.5, 6.5 Hz), 7.32–7.51 (1H, m), 7.67 (4H, s), 9.89–10.07 (1H, m), 10.87–11.05 (1H, m)

EXAMPLE 5-(15)

6-[4-(1-Methyl-2-oxo-1,2,3,4-tetrahydroquinolin-8-yloxyacetamido)phenyl]-5-methyl-4,5-dihydro-1,2,4-triazin-3(2H)-one mp: 146° to 148° C. (dec.)

IR (Nujol): 3220, 3090, 1700 (broad), 1640 cm$^{-1}$

NMR (DMSO-d$_6$, δ): 1.20 (3H, d, J=6 Hz), Ca. 2.3–2.95 (4H, m), 3.38 (3H, s), Ca. 4.4–4.9 (1H, b.m.), 4.79 (2H, s), 6.84–7.1 (3H, m), 7.38 (1H, b.m.), 7.68 (4H, s), 9.89 (1H, b.m.), 10.25 (1H, s)

EXAMPLE 5-(16)

6-(4-D-Mandelylaminophenyl)-5-methyl-4,5-dihydro-1,2,4-triazin-3(2H)-one was obtained by reacting 6-(4-aminophenyl)-5-methyl-4,5-dihydro-1,2,4-triazin-3(2H)-one with 5-phenyl-1,3-dioxolan-2,4-dione according to a similar manner to that of Example 2.

mp: 192° to 194° C. (recrystallized from aqueous ethanol)

NMR (DMSO-d$_6$, δ): 1.21 (3H, d, J=6.5 Hz), 4.65 (1H; d, q; J=3.5, 6.5 Hz), 5.18 (1H, d, J=4.5 Hz), 6.46 (1H, d, J=4.5 Hz), 7.20–8.05 (10H, m), 9.86–10.20 (2H, m)

Anal. Calcd. for $C_{18}H_{18}N_4O_3$: C, 63.89; H, 5.36; N, 16.56; Found: C, 63.85; H, 5.32; N, 16.29

EXAMPLE 5-(17)

6-[4-(N-Methyl-N-n-butyrylamino)phenyl]-5-methyl-4,5-dihydro-1,2,4-triazin-3(2H)-one was obtained by reacting 6-(4-methylaminophenyl)-5-methyl-4,5-dihydro-1,2,4-triazin-3(2H)-one with n-butyric anhydride according to a similar manner to that of Example 2.

NMR (CDCl$_3$, δ): 0.83 (3H, t, J=7 Hz), 1.45 (3H, d, J=7 Hz), 1.3–1.9 (2H, m), 2.13 (2H, t, J=7 Hz), 3.30 (3H, s), 4.74 (1H; d, q; J=3, 7 Hz), 6.83 (1H, b.s.), 7.21 (2H, d, J=8 Hz), 7.76 (2H, d, J=8 Hz), 8.73 (1H, b.s.)

EXAMPLE 5-(18)

6-(4-Acetoacetamidophenyl)-5-methyl-4,5-dihydro-1,2,4-triazin-3(2H)-one was obtained by reacting 6-(4-aminophenyl)-5-methyl-4,5-dihydro-1,2,4-triazin-3(2H)-one with 4-methylene-β-propionolactone according to a similar manner to that of Example 2.

mp: 111° to 114° C. (recrystallized from 50% aqueous ethanol)

IR (Nujol): 3500, 3210, 3060, 1690, 1660 cm$^{-1}$

NMR (DMSO-d6, δ): 1.22 (3H, d, J=6.8 Hz), 1.95 (s) (enol form) 2.24 (s)}(3H), 5.23 (s) (enol form) 3.58 (s)}(2H),
4.63 (1H; d, q; J=3.4, 6.8 Hz), 7.38 (1H, b.s.), 7.59 (2H, d, J=9 Hz), 7.73 (2H, d, J=9 Hz), 9.91 (1H, d, J=2 Hz), 10.18 (1H, b.s.)

EXAMPLE 5-(19)

6-(4-Pyruvoylaminophenyl)-5-methyl-4,5-dihydro-1,2,4-triazin-3(2H)-one was obtained by reacting 6-(4-aminophenyl)-5-methyl-4,5-dihydro-1,2,4-triazin-3(2H)-one with N-pyruvoyloxysuccinimide according to a similar manner to that of Example 2.

mp: 245° to 247° C. (dec.) (recrystallized from aqueous ethanol)

NMR (DMSO-6, δ): 1.20 (3H, d, J=6.8 Hz), 2.44 (3H, s), 4.64 (1H; d, q; J=3.6, 6.8 Hz), 7.39 (1H, b.s.), 7.69 (2H, d, J=9.4 Hz), 7.89 (2H, d, J=9.4 Hz), 9.94 (1H, d, J=1.8 Hz), 10.51 (1H, b.s.)

Anal. Calcd. for $C_{13}H_{14}N_4O_3$: C, 56.93; H, 5.14; N, 20.43; Found: C, 56.97; H, 5.29; N, 20.53

EXAMPLE 6

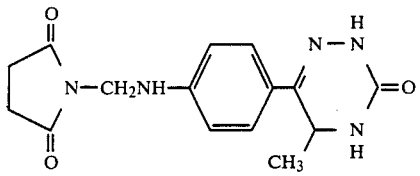

A mixture of 6-(4-aminophenyl)-5-methyl-4,5-dihydro-1,2,4-triazin-3(2H)-one (1.04 g), succinimide (0.61 g) and 36% aqueous formaldehyde (0.47 ml) in ethanol (6 ml) was refluxed for 1.5 hours under stirring. After cooling, the resultant precipitates were collected by filtration, washed with ethanol and recrystallized from a mixture of dimethylsulfoxide (DMSO) and ethanol to give 6-(4-succinimidomethylaminophenyl)-5-methyl-4,5-dihydro-1,2-4-triazin-3(2H)-one (1.14 g).

mp: 238° to 241° C.

NMR (DMSO-d6, δ): 1.17 (3H, d, J=7 Hz), 2.63 (4H, s), 4.55 (1H; d, q; J=3, 7 Hz), 4.81 (2H, d, J=6.4 Hz), 6.84 (2H, d, J=8.5 Hz), 6.7-7.1 (1H, m), 7.26 (1H, b.s.), 7.50 (2H, d, J=8.5 Hz), 9.74 (1H, b.s.)

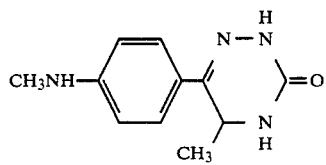

Sodium borohydride (0.766 g) was added portionwise to a stirred solution of the above object compound (6.39 g) of (1) in DMSO (29 ml) at 100° C. After stirring for 15 minutes, the mixture was allowed to cool. The solution was treated with diluted hydrochloric acid to decompose excess sodium borohydride, made alkaline with aqueous sodium bicarbonate and allowed to stand in refrigerator. The precipitates were collected by filtration, washed with water and dried. The filtrate was extracted with ethyl acetate and the extract was washed with water and evaporated in vacuo to give second crop. The combined crude products were washed with an aqueous methanol and dried to give 6-(4-methylaminophenyl)-5-methyl-4,5-dihydro-1,2,4-triazin-3(2H)-one (2.60 g).

NMR (DMSO-d6, δ): 1.19 (3H, d, J=7 Hz), 2.72 (3H, d, J=5 Hz), 4.54 (1H; d, q; J=4, 7 Hz), 6.01 (1H, q, J=5 Hz), 6.56 (2H, d, J=8 Hz), 7.25 (1H, b.s.), 7.50 (2H, d, J=8 Hz), 9.68 (1H, b.s.)

EXAMPLE 7

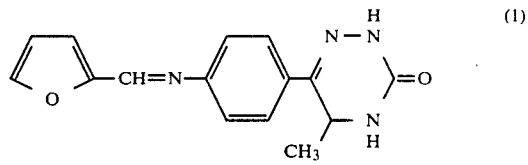

A mixture of 6-(4-aminophenyl)-5-methyl-4,5-dihydro-1,2,4-triazin-3(2H)-one (2 g), furfural (1.41 g), DMF (25 ml) and benzene (25 ml) was refluxed in an apparatus equipped with a Dean-Stark water separator for 3 hours. The reaction mixture was evaporated in vacuo and the resultant residue was triturated with diethyl ether to give 6-[4-(2-furylmethylenamino)phenyl]-5-methyl-4,5-dihydro-1,2,4-triazin-3(2H)-one (2.47 g).

IR (Nujol): 3200, 3100, 1700 cm$^{-1}$

NMR (DMSO-d6, δ): 1.24 (3H, d, J=7 Hz), 4.68 (1H; d, q; J=3, 7 Hz), 6.68 (1H; d, d; J=2, 3 Hz), 7.17 (1H, m), 7.26 (2H, d, J=9 Hz), 7.43 (1H, b.s.), 7.75 (2H, d, J=9 Hz), 7.92 (1H, d, J=2 Hz), 8.45 (1H, s), 10.03 (1H, b.s.)

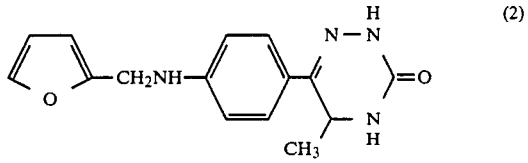

Sodium borohydride (0.318 g) was added portionwise to a stirred mixture of the above obtained compound (2.37 g) of (1) and methanol (24 ml) under ice cooling, and then stirring was continued for 1 hour at room temperature. The mixture was evaporated and the residue was triturated with aqueous methanol. The resulting powder was collected by filtration, washed with water, and recrystallized from 60% aqueous ethanol to give 6-[4-(2-furfurylamino)phenyl]-5-methyl-1,2,4-triazin-3(2H)-one (1.61 g).

mp: 162° to 165° C.

IR (Nujol): 3430, 3200, 3060, 1690, 1605 cm$^{-1}$

NMR (DMSO-d6, δ): 1.18 (3H, d, J=6 Hz), 4.28 (2H, d, J=6 Hz), 4.53 (1H; d, q; J=3.6, 6 Hz), 6.2–6.6 (3H, m), 6.66 (2H, d, J=8.4 Hz), 7.26 (1H, b.s.), 7.47 (2H, d, J=8.4 Hz), 7.54 (1H, b.s.), 9.70 (1H, b.s.)

Anal. Calcd. for $C_{15}H_{16}N_4O_2$: C, 63.37; H, 5.67; N, 19.71; Found: C, 63.17; H, 5.73; N, 19.66

EXAMPLE 8

(1) 6-[4-(3-Pyridylmethylenamino)phenyl]-5-methyl-4,5-dihydro-1,2,4-triazin-3(2H)-one was obtained according to a similar manner to that of Example 7-(1).

IR (Nujol): 3230, 3100, 1710 cm$^{-1}$ (2) 6-[4-(3-Pyridylmethylamino)phenyl]-5-methyl-4,5-dihydro-1,2,4-triazin-3(2H)-one was obtained according to a similar manner to that of Example 7-(2).

mp: 254° to 256° C. (recrystallized from aqueous DMF)

IR (Nujol): 3220, 1685 cm$^{-1}$

NMR (DMSO-d$_6$, δ): 1.16 (3H, d, J=7 Hz), 4.35 (2H, d, J=6 Hz), Ca. 4.3–4.7 (1H, m), 6.59 (2H, d, J=8 Hz), Ca. 6.5–6.8 (1H, m), 7.07–7.6 (2H, m), 7.43 (2H, d, J=8 Hz), 7.73 (1H; t, d; J=2, 8 Hz), 8.42 (1H; d, d; J=2, 5 Hz), 8.56 (1H, d, J=2 Hz), 9.64 (1H, b.s.)

Anal. Calcd. for C$_{16}$H$_{17}$N$_5$O: C, 65.07; H, 5.80; N, 23.71; Found: C, 65.17; H, 5.72; N, 23.90

EXAMPLE 9

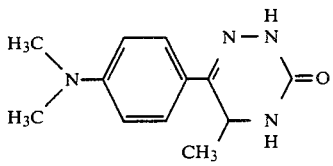

Sodium cyanoborohydride (0.62 g) was added portionwise to a solution of 6-(4-aminophenyl)-5-methyl-4,5-dihydro-1,2,4-triazin-3(2H)-one (1 g) and 36% aqueous formaldehyde (0.92 ml) in a mixture of acetic acid (20 ml) and methanol (30 ml) at room temperature. After stirring for 0.5 hours at the same temperature, the reaction mixture was evaporated in vacuo. To the oily residue was added an aqueous solution of sodium bicarbonate, and the resultant solid was collected by filtration and recrystallized from 70% aqueous ethanol to give 6-(4-dimethylaminophenyl)-5-methyl-4,5-dihydro-1,2,4-triazin-3(2H)-one (0.8 g).

mp: 255° to 261° C.

NMR (DMSO-d$_6$, δ): 1.18 (3H, d, J=6.6 Hz), 2.92 (6H, s), 4.55 (1H; d, q; J=3.2, 6.6 Hz), 6.69 (2H, d, J=8.8 Hz), 7.25 (1H, b.s.), 7.54 (2H, d, J=8.8 Hz), 9.68 (1H, d, J=2.2 Hz)

Anal. Calcd. for C$_{12}$H$_{16}$N$_4$O: C, 62.05; H, 6.94; N, 24.12; Found: C, 62.03; H, 6.85; N, 24.03

EXAMPLE 10

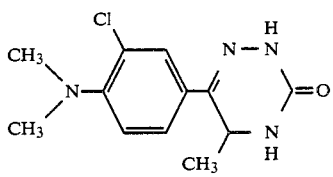

6-(3-Chloro-4-dimethylaminophenyl)-5-methyl-4,5-dihydro-1,2,4-triazin-3(2H)-one (0.66 g) was obtained by alkylating 6-(3-chloro-4-aminophenyl)-5-methyl-4,5-dihydro-1,2,4-triazin-3(2H)-one (1.2 g) with 36% aqueous formaldehyde (0.94 ml) in a similar manner to that of Example 9.

mp: 237° to 244° C. (decomp.) (recrystallized from 70% aqueous ethanol)

IR (Nujol): 3210, 3090, 1700 cm$^{-1}$

NMR (DMSO-d$_6$, δ): 1.20 (3H, d, J=6.6 Hz), 2.77 (6H, s), 4.61 (1H; d, q; J=3.2, 6.6 Hz), 7.11 (1H, d, J=8.2 Hz), 7.40 (1H, b.s.), 7.57 (1H; d, d; J=2.2, 8.2 Hz), 7.70 (1H, d, J=2.2 Hz), 9.93 (1H, d, J=2 Hz)

Anal. Calcd. for C$_{12}$H$_{15}$ClN$_4$O: C, 54.04; H, 5.67; N, 21.01; Found: C, 53.86; H, 5.56; N, 21.22

EXAMPLE 11

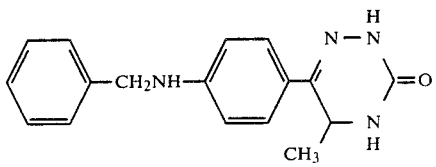

Benzaldehyde (0.25 g) was added to a solution of 6-(4-aminophenyl)-5-methyl-4,5-dihydro-1,2,4-triazin-3(2H)-one (0.48 g) in methanol (45 ml), and the mixture was stirred for 1.5 hours at room temperature. Acetic acid (0.13 ml) was added thereto and then a solution of sodium cyanoborohydride (0.1 g) in methanol (0.7 ml) was added dropwise with stirring. After adding, the reaction mixture was warmed at 50° C. for 2 hours under stirring and evaporated in vacuo. An aqueous solution of sodium bicarbonate was added to the residue and the mixture was triturated to give 6-(4-benzylaminophenyl)-5-methyl-4,5-dihydro-1,2,4-triazin-3(2H)-one (0.68 g).

The physical data of the compound was identical to that of the object compound of Example 37-(4) below.

EXAMPLE 12

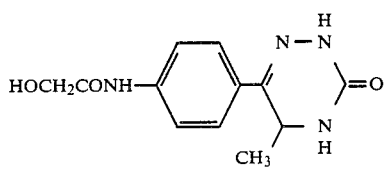

Concentrated ammonia (1.5 ml) was added to a stirred solution of 6-(4-acetoxyacetylaminophenyl)-5-methyl-4,5-dihydro-1,2,4-triazin-3(2H)-one (0.85 g) in methanol (15 ml) and the stirring was continued for 2 hours at room temperature. The resulting precipitates were collected by filtration and recrystallized from 70% aqueous ethanol to give 6-[4-(2-hydroxyacetylamino)phenyl]-5-methyl-4,5-dihydro-1,2,4-triazin-3(2H)-one (0.377 g).

mp: 246° to 248° C.

IR (Nujol): 3200, 1690, 1660 cm$^{-1}$

NMR (DMSO-d$_6$, δ): 1.22 (3H, d, J=7 Hz), 4.03 (2H, d, J=6 Hz), 4.62 (1H; d, q; J=3, 7 Hz), 5.61 (1H, t, J=6 Hz), 7.38 (1H, b.s.), 7.64 (2H, d, J=9 Hz), 7.80 (2H, d, J=9 Hz), 9.75 (1H, b.s.), 9.91 (1H, b.s.)

Anal. Calcd. for C$_{12}$H$_{14}$N$_4$O$_3$: C, 54.96; H, 5.38; N, 21.36; Found: C, 54.90; H, 5.41; N, 21.43

EXAMPLE 13

The following Examples were carried out in a similar manner to that of Example 12.

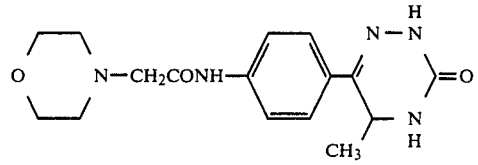

| Example No. | $R_X^2$ | Object Compounds $R_X^1$ | $R_Y^2$ |
|---|---|---|---|
| 13-(1) | H₃CCOOCH₂CH₂CO | H | HOCH₂CH₂CO |
| 13-(2) | H₃CCOOCH₂CO | Br | HOCH₂CO |
| 13-(3) | (D)<br>H₃C—CH—CO<br>\|<br>OCOCH₃ | H | (D)<br>H₃C—CH—CO<br>\|<br>OH |
| 13-(4) | H₅C₂OOC(CH₂)₂CO | H | NaOOC(CH₂)₂CO |
| 13-(5) | H₅C₂OOCCH₂ | H | NaOOCCH₂ |
| 13-(6) | H₅C₂OOCCO | H | NaOOCCO |

The physical data of the above object compounds were as follows.

EXAMPLE 13-(1)

mp: 218° to 219° C. (recrystallized from aqueous ethanol)

NMR (DMSO-d₆, δ): 1.18 (3H, d, J=6.5 Hz), Ca. 2.4–2.7 (2H), 3.72 (2H, q, J=6 Hz), 4.36–4.83 (2H, m), 7.25–7.47 (1H, m), 7.64 (4H, s), 9.84–10.10 (2H, m)

Anal. Calcd. for C₁₃H₁₆N₄O₃: C, 56.51; H, 5.89; N, 20.28; Found: C, 56.54; H, 6.17; N, 19.98

EXAMPLE 13-(2)

mp: 231° to 234° C. (recrystallized from 70% aqueous ethanol)

IR (Nujol): 3310, 3220, 3100, 1750, 1670 cm⁻¹

NMR (DMSO-d₆, δ): 1.21 (3H, d, J=6.2 Hz), 4.08 (2H, d, J=5.4 Hz), 4.67 (1H; d, q; J=3.2, 6.2 Hz), 6.26 (1H, t, J=5.4 Hz), 7.46 (1H, b.s.), 7.73 (1H; d, d; J=2, 8.6 Hz), 8.02 (1H, d, J=2 Hz), 8.32 (1H, d, J=8.6 Hz), 9.40 (1H, s), 10.05 (1H, d, J=1.4 Hz)

EXAMPLE 13-(3)

mp: 234° to 258° C. (recrystallized from aqueous ethanol)

NMR (DMSO-d₆, δ): 1.25 (3H, d, J=6.5 Hz), 1.38 (3H, d, J=6 Hz), 4.26 (1H; d, q; J=5, 6 Hz), 4.72 (1H; d, q; J=3, 6.5 Hz), 5.77 (1H, d, J=5 Hz), 7.34–7.58 (1H, m), 7.58–8.03 (4H, m), 9.67–9.90 (1H, m), 9.90–10.10 (1H, m)

EXAMPLE 13-(4)

mp: 228° to 292° C. (dec.) (recrystallized from 60% aqueous ethanol)

NMR (DMSO-d₆, δ): 1.17 (3H, d, J=6 Hz), Ca. 2.1–2.6 (4H, m), 4.3–4.7 (1H, m), Ca. 7.5 (1H, b.s.), 7.54 (4H, s), 9.86 (1H, b.s.), 10.96 (1H, b.s.)

IR (Nujol): 3390, 3200, 1680, 1575 cm⁻¹

EXAMPLE 13-(5)

mp: >230° C. (dec.)

NMR (DMSO-d₆, δ): 1.16 (3H, d, J=6.4 Hz), 3.38 (2H, s), 4.49 (1H; d, q; J=3, 6.4 Hz), 5.56 (1H, b.s.), 6.49 (2H, d, J=8 Hz), 7.29 (1H, b.s.), 7.37 (2H, d, J=8 Hz), 9.62 (1H, b.s.)

IR (Nujol): 3400, 3240, 1680, 1600, 1580, 1560 cm⁻¹

EXAMPLE 13-(6)

mp: >300° C. (recrystallized from 30% aqueous ethanol)

NMR (DMSO-d₆, δ): 1.18 (3H, d, J=6.4 Hz), 4.36–4.79 (1H, m), 7.35 (1H, b.s.), 7.60 (2H, d, J=9.2 Hz), 7.81 (2H, d, J=9.2 Hz), 9.87 (1H, b.s.), 10.25 (1H, b.s.)

EXAMPLE 14

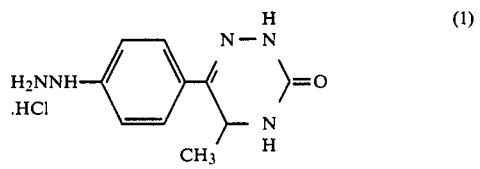

Chloroacetyl chloride (1.25 g) was added dropwise to a solution of 6-(4-aminophenyl)-5-methyl-4,5-dihydro-1,2,4-triazin-3(2H)-one (2.04 g) and triethylamine (1.01 g) in DMF (10 ml) and then stirred for 30 minutes. To the stirred solution were added potassium iodide (0.53 g) and morpholine (4.53 g). The reaction mixture was stirred for 30 minutes and then evaporated in vacuo. To the residue was added water and the resultant solid was collected by filtration, washed with water and recrystallized from aqueous ethanol to give 6-[4-(2-morpholinoacetamido)phenyl]-5-methyl-4,5-dihydro-1,2,4-triazin-3(2H)-one (2.13 g).

mp: 244° to 247° C.

NMR (DMSO-d₆, δ): 1.22 (3H, d, J=6.5 Hz), 2.39–2.72 (4H, m), 3.15 (2H, s), 3.53–3.86 (4H, m), 4.66 (1H; d, q; J=3.5, 6.5 Hz), 7.31–7.55 (1H, b.m.), 7.70 (4H, s), 9.73–10.13 (2H, m)

Anal. Calcd. for C₁₆H₂₁N₅O₃: C, 57.99; H, 6.39; N, 21.13; Found: C, 58.00; H, 6.34; N, 21.09

EXAMPLE 15

(1)

A solution of sodium nitrite (3.6 g) in water (10 ml) was added dropwise to a solution of 6-(4-aminophenyl)-5-methyl-4,5-dihydro-1,2,4-triazin-3(2H)-one (9.8 g) in a mixture of concentrated hydrochloric acid (10 ml) and water (30 ml) at 0° C. After stirring for 0.5 hours, a solution of stannous chloride dihydrate (43.12 g) in conc. hydrochloric acid (43 ml) was added thereto at 0° C. After stirring for 2 hours, the mixture was made alkaline with an aqueous solution of sodium hydroxide and the resultant precipitates were collected by filtration and washed with water. The crude product was dissolved in 10% hydrochloric acid under warming, and then allowed to stand at room temperature. The precipitates were collected by filtration and then dissolved in water. The aqueous solution was washed with ethyl acetate, treated with activated charcoal, and made alkaline with an aqueous solution of sodium hydroxide. The resultant precipitates were collected by filtration, washed with water, and recrystallized from 10% hydrochloric acid to give 6-(4-hyrazinophenyl)-5-methyl-4,5-dihydro-1,2,4-triazin-3(2H)-one hydrochloride (3.2 g).

mp: 235° C. (dec.)

NMR (DMSO-$d_6$, δ): 1.19 (3H, d, J=7.5 Hz), 4.45 (1H; d, q; J=3, 7.5 Hz), 7.02 (2H, d, J=8.5 Hz), 7.26–7.50 (1H, b.m), 7.65 (2H, d, J=8.5 Hz), 7.9–9.0 (1H, b.m), 9.8–10.0 (1H, b.m), 9.7–10.9 (2H, b.m)

A free form compound (1.35 g) of the above hydrochloride compound was obtained by treatment of the mother liquid with an aqueous solution of sodium hydroxide.

NMR (DMSO-$d_6$, δ): 1.19 (3H, d, J=7 Hz), 3.93–4.18 (2H, b.m), 4.54 (1H, d, q; J=4, 7 Hz), 6.77 (2H, d, J=9 Hz), 6.95–7.14 (1H, b.m), 7.14–7.34 (1H, b.m), 7.49 (2H, d, J=9 Hz), 9.57–9.80 (1H, b.m)

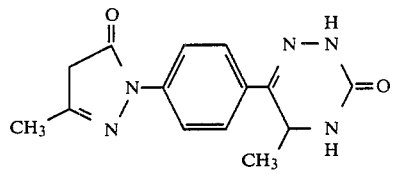

(2)

A mixture of 6-(4-hydrazinophenyl)-5-methyl-4,5-dihydro-1,2,4-triazin-3(2H)-one (0.9 g), methyl acetoacetate (0.5 g) in ethanol (6 ml) and a saturated solution of hydrogen chloride in ethanol (1 drop) was refluxed for 8 hours with stirring and then allowed to stand at room temperature. The resultant precipitates were collected by filtration, washed with ethanol and recrystallized from aqueous ethanol to give isomeric mixture of 6-[4-(4,5-dihydro-3-methyl-5-oxopyrazol-1-yl)phenyl]-5-methyl-4,5-dihydro-1,2,4-triazin-3(2H)-one (0.481 g).

mp: 257° to 260° C. (dec.)

NMR (DMSO-$d_6$, δ): 1.24 (3H, d, J=6.5 Hz), 2.13 (3H, s), 3.66–3.78 (0.3H, m), 4.67 (1H; d, q; J=3.5, 6.5 Hz), 5.37 (0.85H, s), 7.31–7.56 (1H, m), 7.78 (4H, s), 9.94–10.07 (1H, m)

Anal. Calcd. for $C_{14}H_{15}N_5O_2$: C, 58.94; H, 5.30; N, 24.55; Found: C, 58.72; H, 5.23; N, 24.57

EXAMPLE 16

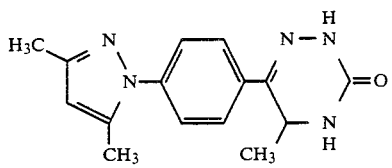

6-[4-(3,5-Dimethylpyrazol-1-yl)phenyl]-5-methyl-4,5-dihydro-1,2,4-triazin-3(2H)-one (0.6 g) was obtained by reacting 6-(4-hydrazinophenyl)-5-methyl-4,5-dihydro-1,2,4-triazin-3(2H)-one (1.13 g) with acetylacetone (0.66 g) according to a similar manner to that of Example 15-(2).

mp: 240° to 241° C. (recrystallized from aqueous ethanol)

NMR (DMSO-$d_6$, δ): 1.23 (3H, d, J=7 Hz), 2.17 (3H, s), 2.39 (3H, s), 4.69 (1H; d, q; J=3.5, 7 Hz), 6.09 (1H, s), 7.37–7.57 (1H, m), 7.53 (2H, d, J=9 Hz), 7.85 (2H, d, J=9 Hz), 10.02–10.15 (1H, m)

Anal. Calcd. for $C_{15}H_{17}N_5O$: C, 63.59; H, 6.05; N, 24.72; Found: C, 63.41; H, 6.10; N, 24.66

EXAMPLE 17

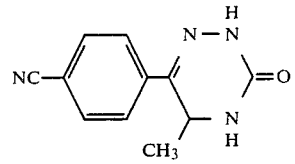

(1)

A solution of sodium nitrite (1.14 g) in water (3 ml) was added dropwise to a solution of 6-(4-aminophenyl)-5-methyl-4,5-dihydro-1,2,4-triazin-3(2H)-one (3.06 g) in a mixture of water (12 ml) and conc. hydrochloric acid (4.5 ml) over a period of 30 minutes under ice cooling. The resultant diazonium solution was cautiously neutralized with a saturated solution of sodium carbonate in water and then a cold mixture of potassium cyanide (1.88 g) and cuprous cyanide (1.17 g) in water (12 ml) was added to the solution. After stirring for 1 hour, the resultant precipitates were collected by filtration, washed successively with water, 1N-sodium hydroxide solution, 1N-hydrochloric acid, water, and then dissolved in aqueous ethanol. The solution was treated with activated charcoal and then evaporated in vacuo. The residue was chromatographed on silica gel (190 g) with a mixture of chloroform and methanol (20:1) as an eluent. The eluents containing object compound were evaporated in vacuo and the residue was recrystallized from aqueous ethanol to give 6-(4-cyanophenyl)-5-methyl-4,5-dihydro-1,2,4-triazin-3(2H)-one (1.469 g).

mp: 268° to 269° C.

NMR (DMSO-$d_6$, δ): 1.22 (3H, d, J=6.8 Hz), 4.73 (1H; d, q; J=3.5, 6.8 Hz), 7.46–7.73 (1H, b.m), 7.89 (4H, s), 10.16–10.43 (1H, b.m)

IR (Nujol): 2220 cm$^{-1}$

Anal. Calcd. for $C_{11}H_{10}N_4O$: C, 62.10; H, 4.84; N, 26.41; Found: C, 61.67; H, 4.70; N, 26.15

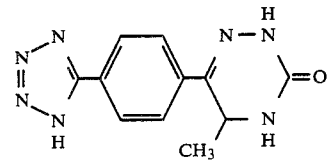

(2)

A mixture of the above object compound (0.49 g) of (1), sodium azide (0.16 g) and ammonium acetate (0.19 g) in DMF (9 ml) was refluxed for 5.5 hours with stirring and then evaporated in vacuo. The residue was dissolved in water, treated with activated charcoal, and then acidified with 10% hydrochloric acid. The resultant precipitates were collected by filtration, washed with water, and recrystallized from aqueous ethanol to give 6-[4-(1H-tetrazol-5-yl)phenyl]-5-methyl-4,5-dihydro-1,2,4-triazin-3(2H)-one (0.347 g).

mp: 153° to 183° C. (dec.)

NMR (DMSO-$d_6$, δ): 1.25 (3H, d, J=6.5 Hz), 4.76 (1H; d, q; J=3, 6.5 Hz), 7.44–7.64 (1H, b.m), 7.95 (2H, d, J=8 Hz), 8.14 (2H, d, J=8 Hz), 10.1–10.3 (1H, b.m)

EXAMPLE 18

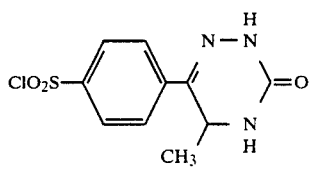

The diazonium salt of 6-(4-aminophenyl)-5-methyl-4,5-dihydro-1,2,4-triazin-3(2H)-one (4.08 g) was obtained in a similar manner to that of Example 15. The diazonium solution was added dropwise to a stirred mixture of cupric chloride dihydrate (0.88 g), water (1.82 ml) and a saturated solution of sulfur dioxide in acetic acid (20 ml) over 10 minutes, and the mixture was stirred at 15° to 17° C. for 1.5 hours. The mixture was filtered by suction and the filtrate was poured into ice water. The resultant precipitates were collected by filtration, dissolved in chloroform, and evaporated in vacuo. The oily residue was triturated with ethyl acetate to give 6-(4-chlorosulfonylphenyl)-5-methyl-4,5-dihydro-1,2,4-triazin-3(2H)-one (4.27 g).

NMR (CDCl$_3$, δ): 1.45 (3H, d, J=6.5 Hz), 4.75 (1H, m), 6.33 (1H, m), 7.90 (2H, d, J=9 Hz), 8.09 (2H, d, J=9 Hz), 8.6 (1H, m)

EXAMPLE 19

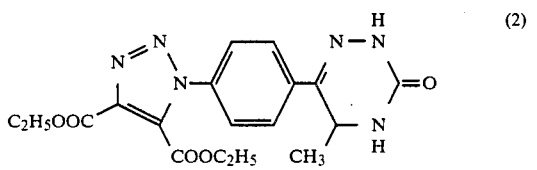

(1)

A solution of sodium nitrite (0.3 g) in water (2 ml) was added dropwise to a solution of 6-(4-hydrazinophenyl)-5-methyl-4,5-dihydro-1,2,4-triazin-3(2H)-one hydrochloride (0.92 g) in a mixture of 1N-hydrochloric acid (3 ml) and water (20 ml) under ice cooling. After stirring for 30 minutes, the resultant precipitates were collected by filtration and washed successively with water, methanol and diisopropyl ether to give 0.56 g of 6-(4-azidophenyl)-5-methyl-4,5-dihydro-1,2,4-triazin-3(2H)-one.

NMR (DMSO-d$_6$, δ): 1.17 (3H, d, J=6.5 Hz), 4.47 (1H; d, q; J=3.5, 6.5 Hz), 7.13 (2H, d, J=8 Hz), 7.31–7.60 (1H, m), 7.77 (2H, d, J=8 Hz), 9.93–10.15 (1H, m)

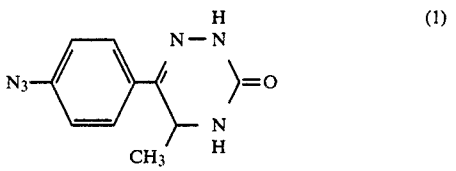

(2)

A mixture of the above object compound (0.5 g) of (1) and diethyl acetylenedicarboxylate (0.37 g) in benzene (15 ml) was refluxed for 34 hours with stirring and then allowed to cool. The solution was chromatographed on silica gel (35 g) with a mixture of chloroform and methanol (100:7) as an eluent. The eluate was evaporated in vacuo and the residue was recrystallized from ethanol to give 6-[4-(4,5-diethoxycarbonyl-1H-1,2,3-triazol-1-yl)phenyl]-5-methyl-4,5-dihydro-1,2,4-triazin-3(2H)-one (0.414 g).

mp: 156° to 157.5° C.

NMR (DMSO-d$_6$, δ): 1.19 (3H, t, J=7 Hz), 1.29 (3H, d, J=6.5 Hz), 1.33 (3H, t, J=7 Hz), 4.34 (2H, q, J=7 Hz), 4.39 (2H, q, J=7 Hz), 4.74 (1H; d, q; J=3, 6.5 Hz), 7.42–7.67 (1H, m), 7.66 (2H, d, J=9 Hz), 7.99 (2H, d, J=9 Hz), 10.16–10.30 (1H, m)

Anal. Calcd. for C$_{18}$H$_{20}$N$_6$O$_5$: C, 54.00 H, 5.03; N, 20.99; Found: C, 53.93; H, 4.96; N, 20.81

EXAMPLE 20

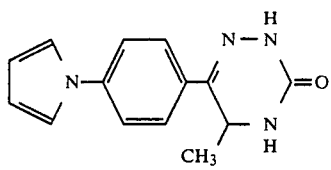

A mixture of 6-(4-aminophenyl)-5-methyl-4,5-dihydro-1,2,4-triazin-3(2H)-one (2.04 g) and 2,5-dimethoxytetrahydrofuran (1.32 g) in acetic acid (6 ml) was refluxed for 45 minutes and the allowed to stand at room temperature. The resultant precipitates were washed with diisopropyl ether and dissolved in a mixture of acetic acid, methanol and chloroform (1:2:50). The solution was chromatographed on silica gel (300 g) with a mixture of chloroform and methanol (10:1) as an eluent. The eluates were evaporated and the residue was crystallized from aqueous DMF to give 6-[4-(1-pyrrolyl)phenyl]-5-methyl-4,5-dihydro-1,2,4-triazin-3(2H)-one (0.97 g).

mp: 269° to 271° C.

NMR (DMSO-d$_6$, δ): 1.22 (3H, d, J=7 Hz), 4.71 (1H; d, q; J=3.2, 7 Hz), 6.28 (2H, t, J=2 Hz), 7.37–7.99 (3H, m), 7.58 (2H, d, J=9 Hz), 7.82 (2H, d, J=9 Hz), 9.97–10.15 (1H, b.m)

Anal. Calcd. for C$_{14}$H$_{14}$N$_4$O: C, 66.13; H, 5.55; N, 22.03; Found: C, 66.45; H, 5.57; N, 22.16

EXAMPLE 21

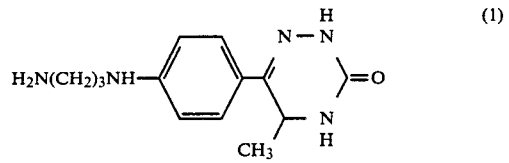

(1)

To a stirred mixture of the object compound (6.5 g) of Example 37(3) and methanol (80 ml) was added 100% hydrazine hydrate (5 ml) at 40° C. under stirring, and the stirring was continued for 30 minutes at room temperature. The solution was evaporated in vacuo and the residue was filtered by suction after addition of methanol thereto. The filtrate was evaporated and the residue was recrystallized from ethanol to give 6-[4-(3-aminopropylamino)phenyl]-5-methyl-4,5-dihyro-1,2,4-triazin-3(2H)-one (1.73 g).

mp: 177.5° to 179° C.

NMR (DMSO-d$_6$, δ): 1.15 (3H, d, J=6 Hz), 1.59 (2H, t, J=6 Hz), 1.89 (2H, b.s.), 2.61 (2H, t, J=6 Hz), 2.8–3.3 (2H, m), 4.48 (1H, broad q, J=6 Hz), 5.89 (1H, broad t, J=5 Hz), 6.48 (2H, d, J=8 Hz), 7.20 (1H, b.s.), 7.36 (2H, d, J=8 Hz), 9.58 (1H, b.s.)

IR (Nujol): 3300, 3200, 1680, 1600 cm$^{-1}$

Anal. Calcd. for $C_{13}H_{19}N_5O$: C, 59.75; H, 7.33; N, 26.80; Found: C, 59,70; H, 7.05; N, 26.55

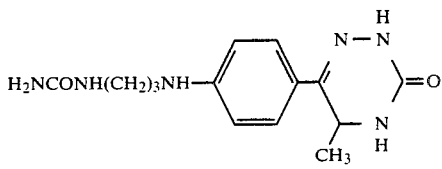
(2)

Potassium cyanate (0.516 g) was added to a solution of 6-[4-(3-aminopropylamino)phenyl]-5-methyl-4,5-dihydro-1,2,4-triazin-3(2H)-one (1.66 g), acetic acid (0.382 g) and methanol (10 ml) in water (20 ml), and the mixture was stirred for 60 hours at room temperature. The resulting precipitates were collected by filtration, washed with water and recrystallized from 80% aqueous ethanol to give 6-[4-(3-ureidopropylamino)phenyl]-5-methyl-4,5-dihydro-1,2,4-triazin-3(2H)-one (0.62 g).

mp: 200° to 202.5° C. (dec.)

IR (Nujol): 3450, 3310, 3180, 1685, 1600 cm$^{-1}$

NMR (DMSO-d$_6$, δ): 1.16 (3H, d, J=6.4 Hz), 1.63 (2H, quintet, J=6.8 Hz), 2.8–3.3 (4H,m), 4.49 (1H; d, q; J=3.6, 6.4 Hz), 5.36 (2H, b.s.), 5.8–6.2 (2H, broad m), 6.56 (2H, d, J=8.4 Hz), 7.19 (1H, b.s.), 7.45 (2H, d, J=8.4 Hz), 9.62 (1H, b.s.)

Anal. Calcd. for $C_{14}H_{20}N_6O_2$: C, 55.25; H, 6.62; N, 27.61; Found: C, 55.35; H, 6.44; N, 27.79

EXAMPLE 22

(1) 6-(4-Acryloylaminophenyl)-5-methyl-4,5-dihydro-1,2,4-triazin-3(2H)-one was obtained by reacting 6-(4-aminophenyl)-5-methyl-4,5-dihydro-1,2,4-triazin-3(2H)-one with acryl chloride according to a similar manner to that of Example 1.

NMR (DMSO-d$_6$, δ): 1.20 (3H, d, J=7 Hz), 4.63 (1H; d, q; J=3, 7 Hz), 5.76 (1H; d, d; J=4.5, 8.5 Hz), 6.35 (1H, d, J=4.5 Hz), 6.39 (1H, d, J=8.5 Hz), 7.29–7.5 (1H, m), 7.69 (4H, s), 9.85–10.01 (1H, m), 10.20–10.31 (1H, m)

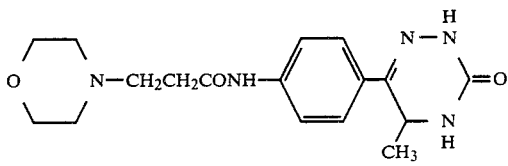
(2)

A mixture of the above object compound (1.01 g) of (1) and morpholine (3.58 g) was heated at 115° for 40 minutes, cooled, and triturated with water. The resultant crystals were collected by filtration, washed with water and then ethyl acetate, and recrystallized from aqueous ethanol to give 6-[4-(3-morpholinopropionamido)phenyl]-5-methyl-4,5-dihydro-1,2,4-triazin-3(2H)-one (0.8 g).

mp: 145° to 149° C.

NMR (DMSO-d$_6$, δ): 1.21 (3H, d, J=6.9 Hz), Ca. 2.3–2.8 (8H, m), 3.47–3.74 (4H, m), 4.60 (1H; d, q; J=3.5, 6.9 Hz), 7.22–7.48 (1H, m), 7.63 (4H, s), 9.76–9.93 (1H, m), 10.04–10.20 (1H, m)

EXAMPLE 23

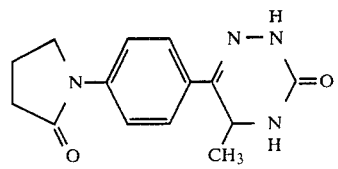

A solution of 6-[4-(4-chlorobutyrylamino)phenyl]-5-methyl-4,5-dihydro-1,2,4-triazin-3(2H)-one (3.879 g) in DMF (38 ml) was added dropwise to a stirred mixture of sodium hydride (1.055 g) in DMF (13 ml) under ice cooling and stirring was continued for 30 minutes. The mixture was evaporated in vacuo after addition of acetic acid (1.85 ml) thereto. Water was added to the residue and the resultant precipitates were collected by filtration and recrystallized 70% aqueous ethanol to give 6-[4-(2oxo-1-pyrrolidinyl)phenyl]-5-methyl-4,5-dihydro-1,2,4-triazin-3(2H)-one (1.77 g).

mp: 278° to 280° C.

NMR (DMSO-d$_6$, δ): 1.19 (3H, d, J=7 Hz), Ca. 1.8–2.3 (2H, m), 2.49 (2H, t, J=6.6 Hz), 3.79 (2H, t, J=6.2 Hz), 4.57 (1H; d, q; J=3.2, 7 Hz), 7.33 (1H, b.s.), 7.63 (4H, s), 9.82 (1H, b.s.)

IR (Nujol): 3220, 3080, 1700 cm$^{-1}$

Anal. Calcd. for $C_{14}H_{16}N_4O_2$: C, 61.75; H, 5.92; N, 20.57; Found: C, 61.82; H, 5.87; N, 20.52

EXAMPLE 24

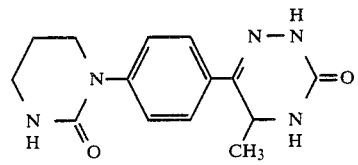

6-[4-(3-Ureidopropylamino)phenyl]-5-methyl-4,5-dihydro-1,2,4-triazin-3(2H)-one (0.96 g) was heated at 220° C. for 2 hours and the resultant solid was recrystallized from aqueous ethanol to give 6-[4-(2-oxoperhydropyrimidin-1-yl)phenyl]-5-methyl-4,5-dihydro-1,2,4-triazin-3(2H)-one (0.43 g).

mp: 304° to 306° C. (dec.)

IR (Nujol): 3200, 3060, 1690, 1645 cm$^{-1}$

NMR (DMSO-d$_6$, δ): 1.20 (3H, d, J=6.4 Hz), 1.8–2.2 (2H, m), Ca. 3.1–3.4 (2H, m), 3,64 (2H, t, J=5.8 Hz), 4.62 (1H; d, q; J=2.6, 6.4 Hz), 6.61 (1H, b.s.), 7.3 (2H, d, J=9 Hz), Ca. 7.4 (1H, b.s.), 7.64 (2H, d, J=9 Hz), 9.91 (1H, b.s.)

Anal. Calcd. for $C_{14}H_{17}N_5O_2$: C, 58.52; H, 5.96; N, 24.37; Found: C, 58.77; H, 6.03; N, 24.31

EXAMPLE 25

(1) A mixture of 4'-benzyloxy-2-hydroxyiminopropiophenone (21.1 g), thiosemicarbazide (7.15 g), methanol (107 ml) and a saturated solution of hydrogen chloride in methanol (2 ml) was refluxed for 65 minutes with stirring. After cooling, the resultant precipitates were collected by filtration, washed successively with methanol, water and methanol, and then dried to give 17.9 g of 4'-benzyloxy-2-hydroxyiminopropiophenone thiosemicarbazone.

NMR (DMSO—d6, δ): 1.93 (s), 2.16 (s) } (3H), 5.17 (2H, s), 7.1–7.6 (9H, m) 8.1 (1H, b.s.), 8.3–8.7 (2H, m), 12.1 (s), 11.66 (s) } (1H)

(2) A mixture of the above obtained thiosemicarbazone (8 g), potassium carbonate (7.4 g) and water (80 ml) was refluxed for 80 minutes with stirring, and the reaction mixture was treated with activted charcoal and filtered by suction. To the filtrate was added dropwise methyl iodide (3.99 g) with stirring and the stirring was continued for 15 minutes at room temperature.

The reaction mixture was extracted with ethyl acetate and the extract was washed with water, dried over magnesium sulfate, and evaporated in vacuo. The oily residue was chromatographed on silica gel (60 g) using chloroform as an eluent. The eluate was evaporated in vacuo and the residual solid was washed with ether and dried to give 6-(4-benzyloxyphenyl)-5-methyl-3-methylthio-1,2,4-triazine (3.77 g).

NMR (CDCl3, δ): 2.53 (3H, s), 2.67 (3H, s), 5.12 (2H, s), 7.08 (2H, d, J=8.6 Hz), Ca. 7.3–7.5 (5H, m), 7.57 (2H, d, J=8.6 Hz)

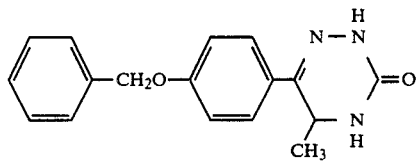

(3)

A mixture of 6-(4-benzyloxyphenyl)-5-methyl-3-methylthio-1,2,4-triazine (3.69 g) in 10% aqueous solution of potassium hydroxide (18 ml) and methanol (36 ml) was heated at 60° for 3.5 hours with stirring and allowed to stand at room temperature. The resultant precipitates were collected by filtration, washed with methanol, and dried to give the potassium salt of 3-hydroxytriazine (3.58 g).

To a suspension of the potassium salt (3.58 g) in hot methanol (70 ml) was added sodium borohydride (0.409 g), stirred for 30 minutes at room temperature, and acidified with concentrated hydrochloride acid. The resultant precipitates were collected by filtration, washed with methanol, and dried to give 3.51 g of 6-(4-benzyloxyphenyl)-5-methyl-4,5-dihydro-1,2,4-triazin-3(2H)-one.

NMR (DMSO-d6, δ) : 1.19 (3H, d, J=6.6 Hz), 4.60 (1H; d, q; J=2.8, 6.6 Hz), 5.13 (2H, s), 7.02 (2H, d, J=9.4 Hz), 7.2–7.5 (6H, m), 7.66 (2H, d, J=9.4 Hz), 9.83 (1H, d, J=2 Hz)

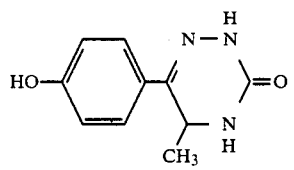

(4)

A solution of the above obtained compound (1.5 g) of (3) in acetic acid (36 ml) was hydrogenated over 5% palladium on carbon (1.6 g) under atmospheric pressure at room temperature. After the theoretical amount of hydrogen gas was absorbed, the catalyst was filtered off, washed with acetic acid, and the filtrate was evaporated in vacuo. To the residue was added water and the resultant solid was recrystallized from 90% aqueous ethanol to give 6-(4-hydroxyphenyl)-5-methyl-4,5-dihydro-1,2,4-triazin-3(2H)-one (0.42 g).

mp: 256° to 259° C.

NMR (DMSO-d6, δ): 1.19 (3H, d, J=7.2 Hz), 4.57 (1H; d, q; J=3.8, 7.2 Hz), 6.80 (2H, d, J=8.4 Hz), 7.31 (1H, b.s.), 7.56 (2H, d, J=8.4 Hz), 9.6–9.8 (2H, m)

Anal. Calcd. for C10H11N3O2: C, 58.53, H, 5.40; N, 20.48; Found: C, 58.41; H, 5.28; N, 20.50

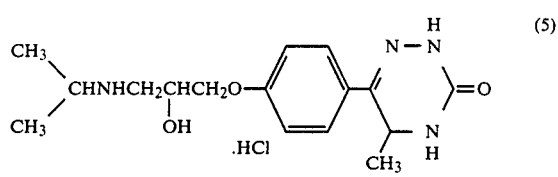

(5)

Epichlorohydrin (0.77 ml) was added to a solution of the above obtained compound (1 g) of (4) and sodium hydroxide (0.24 g) in water (5 ml) and stirred for 29 hours at room temperature. The precipitated oil was separated by decantation, washed with water, and dissolved in isopropylamine (10 ml). The solution was stirred for 16 hours at room temperature and evaporated in vacuo. To the residue was added 10% hydrochloric acid (50 ml) and then filtered by suction. The filtrate was washed with chloroform, treated with activated charcoal, and evaporated in vacuo. The oily residue was dissolved in methanol and evaporated in vacuo. The residue was triturated with diethyl ether to give 6-[4-(2-hydroxy-3-isopropylaminopropoxy)phenyl]-5-methyl-4,5-dihydro-1,2,4-triazin-3(2H)-one hydrochloride (1.28 g), mp 85° to 90° C.

IR (KBr): 3290 (broad), 1670, 1246, 1160 cm$^{-1}$

NMR (DMSO-d6, δ): 1.15 (3H, d, J=6.2 Hz), 1.21 (6H, d, J=7 Hz), 3.07 (2H, m), 3.20 (1H, m), 3.90 (1H, m), 4.06 (2H, s), 4.60 (1H, m), 6.95 (2H, d, J=8.2 Hz), 7.64 (2H, d, J=8.2 Hz), 7.50 (1H, b.s.), 9.00 (2H, m), 9.83 (1H, b.s.)

EXAMPLE 26

(1) 4'-(N-Methylacetamido)-2-hydroxyiminopropiophenone thiosemicarbazone (8.3 g) was obtained from 4'-(N-methylacetoamido)-2-hydroxyiminopropiophenone (7.0 g) according to a similar manner to that of Example 25-(1) except that acetic acid was used instead of a saturated solution of hydrogen chloride in methanol.

NMR (DMSO-d6, δ): 1.69 (3H, s), 2.17 (3H, s), 3.20 (3H, s), 7.23 (2H, d, J=8 Hz), 7.45 (2H, d, J=8 Hz), 8.08 (1H, b.s.), 8.56 (2H, b.s.), 11.69 (1H, s)

(2) 6-[4-(N-Methylacetamido)phenyl]-5-methyl-3-methylthio-1,2,4-triazine (1.33 g) was obtained from the above object compound (4.78 g) of (1) according to a similar manner to that of Example 25-(2) except that crystallization from a residue of eluates was conducted by diethylether.

NMR (DMSO-d6, δ): 1.91 (3H, s), Ca. 2.5 (3H, s), 2.66 (3H, s), 3.25 (3H, s), 7.53 (2H, d, J=8 Hz), 7.80 (2H, d, J=8 Hz)

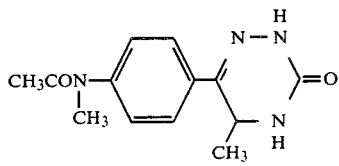

6-[4-(N-Methylacetamido)phenyl]-5-methyl-4,5-dihydro-1,2,4-triazin-3(2H)-one (0.95 g) was obtained from the above obtained compound (1.26 g) of (2) according to a similar manner to that of Example 25-(3) except that the isolation of the object compound was conducted as follows. The reaction mixture was acidified with diluted hydrochloric acid, evaporated in vacuo, and extracted with chloroform. The extract was dried over magnesium sulfate and evaporated. The residue was crystallized from a mixture of benzene and ethanol.

mp: 240° to 243° C.

NMR (DMSO-d$_6$, δ): 1.22 (3H, d, J=7 Hz), 1.86 (3H, s), 3.20 (3H, s), 4.68 (1H, m), 7.36 (2H, d, J=8 Hz), Ca. 7.5 (1H, b.s.), 7.79 (2H, d, J=8 Hz), 10.07 (1H, d, J=2 Hz)

EXAMPLE 27

(1) A mixture of 4'-(N-methylacetamido)-2-hydroxyiminopropiophenone thiosemicarbazone (7.19 g), potassium carbonate (7.21 g) and water (60 ml) was refluxed for 3 hours with stirring. After cooling, the mixture was filtered by suction and sodium chloroacetate (4.09 g) was added to the filtrate at room temperature with stirring. After 1 hour, the solution was washed with methylenechloride and acidified with 10% hydrochloric acid. The mixture was extracted with methylene chloride and the extract was dried over magnesium sulfate and evaporated in vacuo. The resiude was dissolved in ethyl acetate, treated with activated charcoal and evaporated in vacuo to give an oil of 6-[4-(N-methylacetamido)phenyl]-3-carboxymethylthio-5-methyl-1,2,4-triazine (5.11 g).

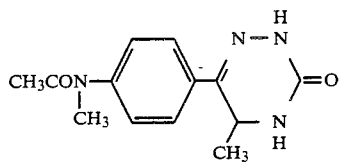

6-[4-(N-Methylacetamido)phenyl]-5-methyl-4,5-dihydro-1,2,4-triazin-3(2H)-one (0.158 g) was obtained from the above obtained compound (0.8 g) according to a substantially same manner to that of Example 25-(3).

mp: 239° to 243° C.

The other physical data were identical with ones of the object compound of Example 26-(3).

EXAMPLE 28

(1) 6-(2-Hydroxyimino-1-thiosemicarbazonopropyl)-1-methyl-2-oxo-1,2,3,4-tetrahydroquinoline (0.34 g) was obtained from 6-(2-hydroxyiminopropionyl)-1-methyl-2-oxo-1,2,3,4-tetrahydroquinoline (1 'g) according to similar manner to that of Example 25-(1).

NMR (DMSO-d$_6$, δ): 2.14 (3H, s), 2.4–3.1 (4H, m), 3.25 (3H, s), 7.0–7.3 (3H, m), 8.07 (1H, b.s.), 8.47 (1H, s), 8.5 (1H, b.s.), 11.68 (1H, s)

(2) 5-Methyl-6-(1-methyl-2-oxo-1,2,3,4-tetrahydroquinolin-6-yl)-3-methylthio-1,2,4-triazine (26.05 g) was obtained from the above compound (56.53 g) according to similar manner to that of Example 25-(2).

NMR (CDCl$_3$, δ): 2.58 (3H, s), 2.69 (3H, s), Ca. 2.5–3.2 (4H, m), 3.4 (3H, s), 7.1 (1H, d, J=9 Hz), 7.4–7.68 (2H, m)

(3) 5-Methyl-6-(1-methyl-2-oxo-1,2,3,4-tetrahydroquinolin-6-yl)-4,5-dihydro-1,2,4-triazin-3(2H)-one (3.45 g) was obtained from the above compound (5.0 g) of (2) according to a similar manner to that of Example 25-(3).

mp: 240° to 242.5° C.

NMR (DMSO-d$_6$, δ): 1.43 (3H, d, J=6 Hz), 2.40–3.10 (4H, m), 3.23 (3H, s), 4.63 (1H; d, q; J=3, 6 Hz) 7.06 (1H; d, J=9.5 Hz), 7.30–7.70 (3H, m), 9.92 (1H, m)

Anal Calcd. for C$_{14}$H$_{16}$N$_4$O$_2$: C, 61.75; H, 5.92; Found: C, 61.80; H, 6.11

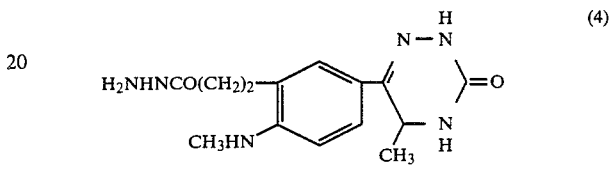

A mixture of 4,5-dihydro-5-methyl-6-(1-methyl-2-oxo-1,2,3,4-tetrahydroquinolin-6-yl)-1,2,4-triazin-3(2H)-one (10 g) and 100% hydrazine hydrate (60 ml) was refluxed for 7 hours under stirring and evaporated in vacuo. The residue was dissolved in a mixture of n-butanol and ethyl acetate and extracted with 5% hydrochloric acid. The extract was washed with ethyl acetate, made alkaline with aqueous sodium bicarbonate, and evaporated in vacuo. The residue was extracted with ethanol and the extract was evaporated in vacuo. The residue was purified by column chromatography on silica gel (50 g) with a mixture of chloroform and methanol (10:1 to 5:1) as a solvent. The eluate was evaporated in vacuo and the residue was triturated in a mixture of chloroform and methanol. The crystals were collected by filtration, washed with chloroform, dried, and recrystallized from an aqueous methanol to give 6-[3-(2-hydroazinocarbonylethyl)-4-methylamino)-phenyl]-5-methyl-4,5-dihydro-1,2,4-triazin-3(2H)-one (2.64 g).

mp: 238° to 239° C. (dec.)

IR (Nujol): 3400, 3300 (shoulder), 3200, 3080, 1690, 1665, 1625, 1605 cm$^{-1}$

NMR (DMSO-d$_6$, δ): 1.19 (3H, d, J=7 Hz), Ca. 2.2 to 2.7 (4H, m), 2.76 (3H, d, J=5 Hz), 4.17 (1H, s), 4.53 (1H; d, q; J=2, 7 Hz), 5.53 (1H, q, J=5 Hz), 6.49 (1H, d, J=9 Hz), Ca. 7.2 to 7.6 (2H, m), 8.96 (1H, b.s.), 9.65 (1H, b.s.)

Anal. Calcd. for C$_{14}$H$_{20}$N$_6$O$_2$: C, 55.25; H, 6.62; N, 27.61; Found: C, 55.25; H, 6.55; N, 27.53

EXAMPLE 29

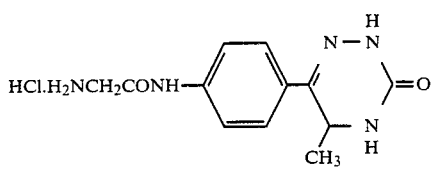

A saturated methanolic solution of hydrogen chloride (7 ml) was added to a suspension of 6-[4-[N-(t-butoxycarbonyl)glycylamino]phenyl]-5-methyl-4,5-dihydro-1,2,4-triazin-3(2H)-one (1.67 g) in methanol (40 ml), and the solution was stirred for 2 hours at ambient temperature. The reaction mixture was evaporated under reduced pressure and the residual solid was recrystallized from methanol to give 0.83 g of 6-(4-glycyclaminophenyl)-5-methyl-4,5-dihydro-1,2,4-triazin-3(2H)-one hydrochloride.

mp: 317° C. (dec.)

NMR (DMSO-d$_6$, δ): 1.20 (3H, d, J=6 Hz), Ca. 3.5-4.2 (2H, m), 4.62 (1H; d, q; J=3, 6 Hz), 7.43 (1H, b.s.), 7.71 (4H, s), 8.38 (2H, b.s.), 9.94 (1H, s), 11.10 (1H, s).

EXAMPLE 30

To a stirred mixture of 6-(4-aminophenyl)-5-methyl-4,5-dihydro-1,2,4-triazin-3(2H)-one (1.0 g) and N,N-dimethylaniline (0.93 ml) in DMF (10 ml) was added dropwise 2-acetoxypropionyl chloride (0.98 g) under ice cooling. The stirring was continued for one night at ambient temperature. The mixture was concentrated under reduced pressure. The residue was extracted with ethyl acetate after addition of saline solution. The extract was washed successively with 1N hydrochloric acid, water and saline solution, dried over magnesium sulfate and evaporated in vacuo. The residue was chromatographed on silica gel (170 ml) with a mixture of chloroform and methanol (10:1) as an eluent. The eluates containing the object compound were evaporated in vacuo to give 1.13 g of 6-[4-(2-acetoxypropionylamino)phenyl]-5-methyl-4,5-dihydro-1,2,4-triazin-3(2H)-one.

IR (Nujol): 3250, 3100, 1736, 1702, 1687, 1457, 1240, 760 cm$^{-1}$

NMR (CDCl$_3$, δ): 1.29 (3H, d, J=6.4 Hz), 1.58 (3H, d, J=6.8 Hz), 2.17 (3H, s), 4.58 (1H, m), 5.24 (1H, q, J=6.8 Hz), 7.12 (1H, s), 7.56 (4H, s), 8.75 (1H, br s), 9.35 (1H, br s)

EXAMPLE 31

6-[4-(2-L-acetoxypropionylamino)phenyl]-5-methyl-4,5-dihydro-1,2,4-triazin-3(2H)-one (1.04 g) was obtained from 6-(4-aminophenyl)-5-methyl-4,5-dihydro-1,2,4-triazin-3(2H)-one (1.26 g) and 2-L-acetoxypropionyl chloride (1.11 g) according to a similar manner to that of Example 30.

[α]$_D$: −31.39° C. (C=1.3 in chloroform)

IR (Nujol): 3230, 3100, 1732, 1700, 1680, 1460, 1242, 760 cm$^{-1}$

NMR (CDCl$_3$, δ): 1.29 (3H, d, J=6.2 Hz), 1.57 (3H, d, J=7.0 Hz), 2.17 (3H, s), 4.60 (1H, m), 5.29 (1H, q, J=7.0 Hz), 7.15 (1H, br s), 7.52 (4H, s), 8.79 (1H, br s), 9.43 (1H, br s)

EXAMPLE 32

(1) 6-(4-Chloroacetylaminophenyl)-5-methyl-4,5-dihydro-1,2,4-triazin-3(2H)-one (10.18 g) was obtained from 6-(4-aminophenyl)-5-methyl-4,5-dihydro-1,2,4-triazin-3(2H)-one (8.16 g) and chloroacetyl chloride (4.97 g) according to a similar manner to that of Example 30.

IR (Nujol): 3270, 3210, 3080, 1695, 1680 cm$^{-1}$ (2) A mixture of the above obtained compound (2.80 g) of (1), 1-(2-hydroxyethyl)piperazine (1.56 g), potassium carbonate (0.83 g) and sodium iodide (0.75 g) in DMF (15 ml) was stirred for one night at ambient temperature. After addition of chloroform, resulting precipitates were collected by filtration. The filtrates were concentrated under reduced pressure to give a residue. The residue was dissolved in 5% hydrochloric acid, washed with ethyl acetate, made alkaline with sodium carbonate and allowed to stand in refrigerator. The precipitates were collected by filtration, washed with water and dried. The precipitates were combined, recrystallized from a mixture of chloroform and methanol to give 1.81 g of 6-[4-[4-(2-hydroxyethyl)piperazin-1-ylacetylamino]phenyl]-5-methyl-4,5-dihydro-1,2,4-triazin-3(2H)-one.

mp: 230°-232° C. (dec.)

IR (Nujol): 3300, 3200, 3100, 1690 cm$^{-1}$

NMR (DMSO-d$_6$, δ): 1.22 (3H, d, J=7 Hz), 2.3-2.7 (10H, m), 3.13 (2H, s), 3.53 (2H, q, J=6 Hz), 4.33 (1H, t, J=6 Hz), 4.47-4.77 (1H, m), 7.4 (1H, br s), 7.71 (4H, s), 9.78 (1H, s), 9.93 (1H, br s)

Anal. Calcd. for C$_{18}$H$_{26}$N$_6$O$_3$: C, 57.74; H, 7.00; N, 22.44; Found: C, 57.38; H, 6.86; N, 22.54

EXAMPLE 33

The following compounds were obtained according to a similar manner to that of Example 32-(2).

(1) 6-[4-(N,N-Diisopropylglycylamino)phenyl]-5-methyl-4,5-dihydro-1,2,4-triazin-3(2H)-one (yield 80.3%)

mp: 245° to 248° C. (dec.)

IR (Nujol): 3210, 3100, 1700 cm$^{-1}$

NMR (DMOS-d$_6$, δ): 1.04 (12H, d, J=7 Hz), 1.25 (3H, d, J=7 Hz), 2.85-3.25 (2H, m), 3.13 (2H, s), 4.67 (1H, dd, J=4 Hz, 7Hz), 7.43 (1H, br s), 7.73 (4H, s), 9.67 (1H, s)

Anal. Calcd. for C$_{18}$H$_{27}$N$_5$O$_2$: C, 62.59; H, 7.88; N, 20.27; Found: C, 62.04; H, 7.68; N, 20.32

(2) 6-[4-(1-Pyrrolidinoacetylamino)phenyl]-5-methyl-4,5-dihydro-1,2,4-triazin-3(2H)-one (yield 56.0%)

mp: 231° to 233° C.

IR (Nujol): 3300, 1690, 1680, 1660 cm$^{-1}$

NMR (DMSO-d$_6$, δ): 1.21 (3H, d, J=7 Hz), 1.4-2.0 (4H, m), 2.3-2.7 (4H, m), 3.26 (2H, s), 4.4-4.76 (1H, m), 7.38 (1H, br s), 7.72 (4H, s), 9.80 (1H, s), 9.91 (1H, br s)

Anal. Calcd. for C$_{16}$H$_{21}$N$_5$O$_2$: C, 60.94; H, 6.71; N, 22.21; Found: C, 61.01; H, 6.62; N, 22.20

(3) 6-[4-[4-(2-Furoyl)piperazin-1-yl-acetylamino]-phenyl]-5-methyl-4,5-dihydro-1,2,4-triazin-3(2H)-one (yield 71.5%)

mp: 233° to 234° C.

IR (Nujol): 3270, 3200, 3080, 1700, 1695, 1680, 1610 cm$^{-1}$

NMR (DMSO-d$_6$, δ): 1.21 (3H, d, J=7 Hz), 2.4-2.8 (4H, m), 3.21 (2H, s), 3.74 (4H, bt, J=4 Hz), 4.61 (1H, d, q, J=3 Hz, 7 Hz), 6.53-6.68 (1H, m), 6.89-7.05 (1H, m), 7.36 (1H, br s), 7.66 (4H, s), 7.76-7.86 (1H, m), 9.90 (1H, d, J=2 Hz)

Anal. Calcd. for C$_{21}$H$_{24}$N$_6$O$_4$: C, 59.42; H, 5.70; N, 19.80; Found: C, 59.42; H, 5.65; N, 19.81

(4) 6-[4-(N,N-Dimethylglycyclamino)phenyl]-5-methyl-4,5-dihydro-1,2,4-triazin-3(2H)-one (yield 50.4%)

mp: 228° to 230° C. (dec.)

IR (Nujol): 3300, 3200, 3100, 1690, 1620 cm$^{-1}$

NMR (DMSO-d$_6$, δ): 1.21 (3H, d, J=7 Hz), 2.29 (6H, s), 3.08 (2H, s), 4.62 (1H, d, q, J=3 Hz, 7 Hz), 7.38 (1H, br s), 7.68 (4H, s), 9.81 (1H, s), 9.91 (1H, br s)

Anal. Calcd. for C$_{14}$H$_{19}$N$_5$O$_2$: C, 58.12; H, 6.62; N, 24.20; Found: C, 57.93; H, 6.53; N, 23.78

EXAMPLE 34

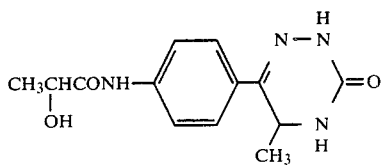

To a stirred solution of 6-[4-(2-acetoxypropionylamino)phenyl]-5-methyl-4,5-dihydro-1,2,4-triazin-3(2H)-one (0.94 g) in methanol (6 ml) was added dropwise 1N sodium hydroxide (3 ml) under ice cooling. The mixture was stirred for 15 minutes after adding water. The resulting precipitates were collected by filtration, washed with water and dried to give 0.61 g of 6-(4-lactoylaminophenyl)-5-methyl-4,5-dihydro-1,2,4-triazin-3(2H)-one.

mp: 217° to 225° C.

IR (Nujol): 3340, 3300, 3260, 1702, 1658, 1520, 1460, 1121 cm$^{-1}$

NMR (DMSO-d$_6$, δ): 1.20 (3H, d, J=7 Hz), 1.31 (3H, d, J=7 Hz), 3.95–4.37 (1H, m), 4.33–4.88 (1H, m), 5.70 (1H, d, J=5 Hz), 7.35 (1H, br s), 7.4–7.9 (4H, m), 9.69 (1H, s), 9.85 (1H, d, J=2 Hz)

Anal. Calcd. for $C_{13}H_{16}N_4O_3$: C, 56.51; H, 5.84; N, 20.28; Found: C, 56.74; H, 5.91; N, 20.33

EXAMPLE 35

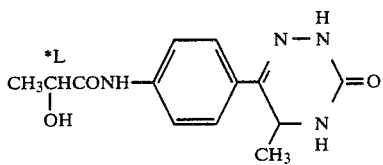

6-(4-L-Lactoylaminophenyl)-5-methyl-4,5-dihydro-1,2,4-triazin-3(2H)-one (0.2 g) was obtained from 6-[4-(2-L-acetoxypropionylamino)phenyl]-5-methyl-4,5-dihydro-1,2,4-triazin-3(2H)-one (0.3 g) according to a similar manner to that of Example 34.

mp: 232° to 241° C.

IR (Nujol): 3340, 3300, 3260, 1693, 1655, 1523, 1460, 1120 cm$^{-1}$

NMR (DMSO-d$_6$, δ): 1.19 (3H, d, J=6.8 Hz), 1.32 (3H, d, J=6.8 Hz), 3.87–4.45 (1H, m), 4.36–4.87 (1H, m), 5.69 (1H, d, J=5.0 Hz), 7.35 (1H, br s), 7.5–7.9 (4H, m), 9.72 (1H, s), 9.87 (1H, d)

Anal. Calcd. for $C_{13}H_{16}N_4O_3$: C, 56.51; H, 5.84; N, 20.28; Found: C, 56.41; H, 5.79; N, 20.30

EXAMPLE 36

The following compounds are obtained according to a similar manner to that of Preparation 1-(3) or Example 25-(3).

(1)
6-[4-[N-(t-Butoxycarbonyl)glycylamino]phenyl]-5-methyl-4,5-dihydro-1,2,4-triazin-3(2H)-one NMR (DMSO-d$_6$, δ): 1.22 (3H, d, J=6.2 Hz), 1.40 (9H, s), 3.76 (2H, d, J=5.8 Hz), 4.62 (1H; d, q; J=2.8, 6.2 Hz), 6.96 (1H, br s), 7.36 (1H, br s), 7.65 (4H, s), 9.90 (1H, br s), 10.00 (1H, br s)

(2)
6-(4-Pyrrolidinophenyl)-5-methyl-4,5-dihydro-1,2,4-triazin-3(2H)-one mp: 276° to 281° C.

NMR (DMSO-d$_6$, δ): 1.17 (3H, d, J=7 Hz), 1.8–2.1 (4H, m), Ca. 3.1–3.4 (4H, m), 4.53 (1H; d, q; J=3, 7 Hz), 6.53 (2H, d, J=8 Hz), 7.22 (1H, br s), 7.47 (2H, d, J=8 Hz), 9.58 (1H, br s)

(3)
6-[4-(2-Methoxyethylamino)phenyl]-5-methyl-4,5-dihydro-1,2,4-triazin-3(2H)-one mp: 160° to 165° C.

NMR (DMSO-d$_6$, δ): 1.17 (3H, d, J=6.8 Hz), 3.1–3.7 (7H, m), 4.50 (1H; d, q; 3.6, 6.8 Hz), 6.59 (2H, d, J=9 Hz), 7.20 (1H, br s), 7.45 (2H, d, J=9 Hz), 9.64 (1H, br s)

(4)
6-(3-Chloro-4-pyruvoylaminophenyl)-5-methyl-4,5-dihydro-1,2,4-triazin-3(2H)-one mp: 283° to 287° C. (dec.)

IR (Nujol): 3340, 3210, 3090, 1710, 1700, 1690 cm$^{-1}$

NMR (DMSO-d$_6$, δ): 1.21 (3H, d, J=6.4 Hz), Ca. 2.4–2.7 (3H, s), 4.69 (1H; d, q; J=3.2, 6.4 Hz), 7.50 (1H, br s), 7.72 (1H; d, d; J=2.2, 8.6 Hz), 7.87 (1H, d, J=2.2 Hz), 8.08 (1H, d, J=8.6 Hz), 9.76 (1H, br s), 10.11 (1H, d, J=2 Hz)

(5)
6-(4-Nicotinamidophenyl)-5-methyl-4,5-dihydro-1,2,4-triazin-3(2H)-one mp: 288° to 290° C.

IR (Nujol): 3350, 3200, 3080, 1700, 1655 cm$^{-1}$

NMR (DMSO-d$_6$, δ): 1.22 (3H, d, J=7 Hz), 4.64 (1H; d, q; J=3, 7 Hz), 7.43 (1H, br s), Ca. 7.5–7.7 (1H, m), 7.77 (4H, s), 8.28 (1H; t, d; J=2, 8 Hz), 8.73 (1H; d, d; J=2, 5 Hz), 9.10 (1H, d, J=2 Hz), 9.92 (1H, br s), 10.50 (1H, s)

(6)
6-[4-(2-Chloropropionylamino)phenyl]-5-methyl-4,5-dihydro-1,2,4-triazin-3(2H)-one mp: 213° to 215° C.

NMR (DMSO-d$_6$, δ): 1.22 (3H, d, J=7 Hz), 1.64 (3H, d, J=7 Hz), Ca. 4.4–4.8 (1H, m), 4.66 (1H, q, J=7 Hz), 7.41 (1H, br s), 7.75 (4H, s), 9.92 (1H, br s), 10.40 (1H, br s)

(7)
6-[4-(4-Chlorobutyrylamino)phenyl]-5-methyl-4,5-dihydro-1,2,4-triazin-3(2H)-one NMR (DMSO-d$_6$, δ): 1.22 (3H, t, J=7 Hz), 1.79–2.36 (2H, m), 2.36–2.73 (2H, complex), 3.71 (2H, t, J=6 Hz), 4.62 (1H; d, q; J=3, 7 Hz), 7.36 (1H, br s), 7.66 (4H, s), 9.89 (1H, br s), 10.07 (1H, s)

(8)
6-[4-(N-Methyl-N-benzoylamino)phenyl]-5-metyyl-4,5-dihydro-1,2,4-triazin-3(2H)-one mp: 135° to 138° C.

NMR (DMSO-d$_6$, δ): 1.14 (3H, d, J=7 Hz), 3.38 (3H, s), Ca. 4.5–4.7 (1H, m), Ca. 7.2 (2H, d, J=8 Hz), 7.26 (5H, s), Ca. 7.4 (1H, br s), 7.63 (2H, d, J=8 Hz), 9.96 (1H, d, J=1.4 Hz)

(9)
6-[4-(N-Methyl-N-cinnamoylamino)phenyl]-5-methyl-4,5-dihydro-1,2,4-triazin-3(2H)-one mp: 125° to 128° C. (dec.)

NMR (DMSO-$d_6$, $\delta$): 1.26 (3H, d, J=7 Hz), 3.35 (3H, s), 4.70 (1H; d, q; J=3, 7 Hz), 6.50 (1H, d, J=15.5 Hz), 7.37 (2H, d, J=8.6 Hz), 7.38 (5H, s), Ca. 7.3–7.6 (1H, br s), Ca. 7.6 (1H, d, J=15.5Hz), 7.85 (2H, d, J=8.6 Hz), 10.13 (1H, br s)

(10)
6-(4-Propioloylaminophenyl)-5-methyl-4,5-dihydro-1,2,4-traizin-3(2H)-one mp: 243° C. (dec.)

NMR (DMSO-$d_6$, $\delta$): 1.20 (3H, d, J=6.5 Hz), 4.43 (1H, s), 4.64 (1H; d, q; J=3.5, 6.5 Hz), 7.32–7.51 (1H, m), 7.67 (4H, s), 9.89–10.07 (1H, m), 10.87–11.05 (1H, m)

(11)
6-[4-(1-Methyl-2-oxo-1,2,4-tetrahydroquinolin-8-yloxyacetamido)phenyl]-5-methyl-4,5-dihydro-1,2,4-traizin-3(2H)-one mp: 146° to 148° C. (dec.)

IR (Nujol): 3220, 3090, 1700 (broad), 1640 cm$^{-1}$

NMR (DMSO-$d_6$, $\delta$): 1.20 (3H, d, J=6 Hz), Ca. 2.3–2.95 (4H, m), 3.38 (3H, s), Ca. 4.4–4.9 (1H, b.m), 4.79 (2H, s), 6.84–7.1 (3H, m), 7.38 (1H, b.m.), 7.68 (4H, s), 9.89 (1H, b.m.), 10.25 (1H, s)

(12)
6-(4-n-Butylaminophenyl)-5-methyl-4,5-dihydro-1,2,4-triazin-3(2H)-one mp: 183° to 186.5° C.

NMR (DMSO-$d_6$, $\delta$): 0.7–1.9 (10H, m), 2.9–3.3 (2H, m), 4.54 (1H; d, q; J=3, 6 Hz), 5.95 (1H, t, J=5.6 Hz), 6.59 (2H, d, J=8.4 Hz), 7.25 (1H, br s), 7.49 (2H, d, J=8.4 Hz), 9.68 (1H, br s)

(13)
6-[4-(2-Hydroxyethylamino)phenyl]-5-methyl-4,5-dihydro-1,2,4-triazin-3(2H)-one mp: 182° to 185° C.

NMR (DMSO-$d_6$, $\delta$): 1.15 (3H, d, J=6 Hz), 3.10 (2H, t, J=6 Hz), 3.53 (2H, t, J=6 Hz), 3.9–4.7 (3H, m), 6.55 (2H, d, J=8.8 Hz), 7.18 (1H, br s), 7.41 (2H, d, J=8.8 Hz), 9.58 (1H, br s)

(14)
6-(4-Benzylaminophenyl)-5-methyl-4,5-dihydro-1,2,4-triazin-3(2H)-one mp: 193° to 194° C.

NMR (DMSO-$d_6$, $\delta$): 1.16 (3H, d, J=7 Hz), 4.31 (2H, d, J=6 Hz), 4.50 (1H; d, q; J=3.8, 7 Hz), 6.59 (2H, d, J=8.2 Hz), 6.61 (1H, br s), 7.3–7.6 (8H, m), 9.69 (1H, br s)

(15)
6-[4-[N,N-Di(2-propynyl)amino]phenyl]-5-methyl-4,5-dihydro-1,2,4-triazin-3(2H)-one mp: 191° to 193° C.

NMR (DMSO-$d_6$, $\delta$): 1.18 (3H, d, J=6.5 Hz), 3.14 (2H, t, J=2 Hz), 4.8 (4H, d, J=2 Hz), 4.59 (1H; d, q; J=3, 6.5 Hz), 6.94 (2H, d, J=9 Hz), 7.22–7.46 (1H, b.m.), 7.63 (2H, d, J=9 Hz), 9.66–9.9 (1H, b.m.))

(16)
6-[4-(2-Propynyl)aminophenyl]-5-methyl-4,5-dihydro-1,2,4-triazin-3(2H)-one mp: 221° to 224° C.

NMR (DMSO-$d_6$, $\delta$): 1.17 (3H, d, J=7 Hz), 3.04 (1H, t, J=2 Hz), 3.90 (2H, d, d; J=2, 6 Hz), 4.54 (1H; d, q; J=3.5, 7 Hz), 6.32 (1H, t, J=6 Hz), 6.64 (2H, d, J=8.5 Hz), 7.12–7.36 (1H, b.m.), 7.50 (2H, d, J=8.5 Hz), 9.55–9.84 (1H, b.m.)

(17)
6-[4-(2-Pyridylamino)phenyl]-5-methyl-4,5-dihydro-1,2,4-triazin-3(2H)-one mp: 254° to 255° C. (dec.)

IR (Nujol): 3200, 3080, 1690, 1620 cm$^{-1}$

NMR (DMSO-$d_6$, $\delta$): 1.22 (3H, d, J=7Hz), 4.61 (1H, d, q; J=2, 7 Hz), 6.64–7.07 (2H, m), 7.33 (1H, b.m.), 7.43–7.91 (5H, m), 8.19 (1H; d, d; J=2, 5 Hz), 9.20 (1H, s), 9.80 (1H, b.m.)

(18)
6-[4-[2-(2-Methoxyethoxy)ethylamino]phenyl]-5-methyl-4,5-dihydro-1,2,4-triazin-3(2H)-one mp: 130° to 135° C.

NMR (DMSO-$d_6$, $\delta$): 1.18 (3H, d, J=6.4 Hz), 3.1–3.4 (2H, m), Ca. 3.3 (3H, s), 3.4–3.8 (6H, m), 4.52 (1H; d, q; J=3, 6.4 Hz), 5.92 (1H, t, J=4Hz), 6.60 (2H, d, J=8.4 Hz), 7.21 (1H, br s), 7.47 (2H, d, J=8.4 Hz), 9.63 (1H, d, J=1.4 Hz)

(19)
6-(4-Morpholionphenyl)-5-methyl-4,5-dihydro-1,2,4-triazin-3(2H)-one mp: 256° to 261° C.

NMR (DMSO-$d_6$, $\delta$): 1.17 (3H, d, J=6.4 Hz), 2.9–3.4 (4H, m), 3.6–3.9 (4H, m), 4.53 (1H; d, q; J=3.4, 6.4 Hz), 6.86 (2H, d, J=9.4 Hz), 7.22 (1H, br s), 7.52 (2H, d, J=9.4 Hz), 9.68 (1H, d, J=2.2 Hz)

(20)
6-(4-D-Mandelylaminophenyl)-5-methyl-4,5-dihydro-1,2,4-triazin-3(2H)-one mp: 192° to 194° C.

NMR (DMSO-$d_6$, $\delta$): 1.21 (3H, d, J=6.5 Hz), 4.65 (1H; d, q; J=3.5, 6.5 Hz), 5.18 (1H, d, J=4.5 Hz), 6.46 (1H, d, J=4.5 Hz), 7.20–8.05 (10H, m), 9.86–10.20 (2H, m)

(21)
6-[4-(N-Methyl-N-n-butyrylamino)phenyl]-5-methyl-4,5-dihydro-1,2,4-triazin-3(2H)-one NMR (CDCl$_3$, $\delta$): 0.83 (3H, t, J=7 Hz), 1.45 (3H, d, J=7 Hz), 1.3–1.9 (2H, m), 2.13 (2H, t, J=7 Hz), 3.30 (3H, s), 4.74 (1H; d, q; J=3, 7 Hz), 6.83 (1H, br s), 7.21 (2H, d, J=8 Hz), 7.76 (2H, d, J=8 Hz), 8.73 (1H, br s)

(22)
6-(4-Methylaminophenyl)-5-methyl-4,5-dihydro-1,2,4-triazin-3-(2H)-one

NMR (DMSO-$d_6$, $\delta$): 1.19 (3H, d, J=7Hz), 2.72 (3H, d, J=5 Hz), 4.54 (1H, d, q; J=4, 7 Hz), 6.01 (1H, q, J=5 Hz), 6.56 (2H, d, J=8 Hz), 7.25 (1H, br s), 7.50 (2H, d, J=8 Hz), 9.68 (1H, br s)

(23)

6-[4-(2-Furfurylamino)phenyl]-5-methyl-1,2,4-triazin-3(2H)-one mp: 162° to 165° C.
IR (Nujol): 3430, 3200, 3060, 1690, 1605 cm$^{-1}$
NMR (DMSO-d$_6$, δ): 1.18 (3H, d, J=6 Hz), 4.28 (2H, d, J=6 Hz), 4.53 (1H; d, q; J=3.6, 6 Hz) 6.2–6.6 (3H, m), 6.66 (2H, d, J=8.4 Hz), 7.26 (1H, br s), 7.47 (2H, d, J=8.4 Hz), 7.54 (1H, br s), 9.70 (1H, br s)

(24) 6-[4-(3-Pyridylmethylamino)phenyl]-5-methyl 4,5-dihydro-1,2,4-triazin-3(2H)-one mp: 254° to 256° C.
IR (Nujol): 3220, 1685 cm$^{-1}$
NMR (DMSO-d$_6$, δ): 1.16 (3H, d, J=7 Hz), 4.35 (2H, d, J=6Hz), Ca. 4.3–4.7 (1H, m), 6.59 (2H, d, J=8 Hz), Ca. 6.5–6.8 (1H, m), 7.07–7.6 (2H, m), 7.43 (2H, d, J=8 Hz), 7.73 (1H; t, d; J=2, 8 Hz), 8.42 (1H; d, d; J=2, 5 Hz), 8.56 (1H, d, J=2 Hz), 9.64 (1H, br s)

(25)

6-(4-Dimethylaminophenyl)-5-methyl-4,5-dihydro-1,2,4-triazin-3(2H)-one mp: 255° to 261° C.
NMR (DMSO-d$_6$, δ): 1.18 (3H, d, J=6.6 Hz), 2.92 (6H, s), 4.55 (1H; d, q; J=3.2, 6.6 Hz), 6.69 (2H, d, J=8.8 Hz), 7.25 (1H, br s), 7.54 (2H, d, J=8.8 Hz), 9.68 (1H, d, J=2.2 Hz)

(26)

6-(3-Chloro-4-dimethylaminophenyl)-5-methyl-4,5-dihydro-1,2,4-triazin-3(2H)-one mp: 237° to 244° C. (dec.)
IR (Nujol): 3210, 3090, 1700 cm$^{-1}$
NMR (DMSO-d$_6$, δ): 1.20 (3H, d, J=6.6 Hz), 2.77 (6H, s), 4.61 (1H, d, q; J=3.2, 6.6 Hz), 7.11 (1H, d, J=8.2 Hz), 7.40 (1H, br s), 7.57 (1H; d, d; J=2.2, 8.2 Hz), 7.70 (1H, d, J=2.2 Hz), 9.93 (1H, d, J=2 Hz)

(27)

6-[4-(2-Hydroxyacetylamino)phenyl]-5-methyl-4,5-dihydro-1,2,4-triazin-3(2H)-one mp: 246° to 248° C.
IR (Nujol): 3200, 1690, 1660 cm$^{-1}$
NMR (DMSO-d$_6$, δ): 1.22 (3H, d, J=7 Hz), 4.03 (2H, d, J=6 Hz), 4.62 (1H; d, q; J=3, 7 Hz), 5.61 (1H, t, J=6 Hz), 7.38 (1H, br s), 7.64 (2H, d, J=9 Hz), 7.80 (2H, d, J=9 Hz), 9.75 (1H, br s), 9.91 (1H, br s)

(28)

6-[4-(3-Hydroxypropionylamino)phenyl]-5-methyl-4,5-dihydro-1,2,4-triazin-3(2H)-one mp: 218° to 219° C.
NMR (DMSO-d$_6$, δ): 1.18 (3H, d, J=6.5 Hz), Ca. 2.4–2.7 (2H), 3.72 (2H, q, J=6 Hz), 4.36–4.83 (2H, m), 7.25–7.47 (1H, m), 7.64 (4H, s), 9.84–10.10 (2H, m)

(29)

6-(3-Bromo-4-glycoloylaminophenyl)-5-methyl-4,5-dihydro-1,2,4-triazin-3(2H)-one mp: 231° to 234° C.
IR (Nujol): 3310, 3320, 3100, 1750, 1670 cm$^{-1}$
NMR (DMSO-d$_6$, δ): 1.21 (3H, d, J=6.2Hz), 4.08 (2H, d, J=5.4Hz), 4.67 (1H, d, q; J=3.2, 6.2 Hz), 6.26 (1H, t, J=5.4 Hz), 7.46 (1H, br s), 7.73 (1H; d, d; J=2, 8.6 Hz), 8.02 (1H, d, J=2Hz), 8.32 (1H, d, J=8.6 Hz), 9.40 (1H, s), 10.05 (1H, d, J=1.4 Hz)

(30)

6-(4-D-Lactoylaminophenyl)-5-methyl-4,5-dihydro-1,2,4-triazin-3(2H)-one mp: 234° to 258° C.
NMR (DMSO-d$_6$, δ): 1.25 (3H, d, J=6.5 Hz), 1.38 (3H, d, J=6 Hz), 4.26 (1H; d, q; J=5, 6 Hz), 4.72 (1H; d, q; J=3, 6.5 Hz), 5.77 (1H, d, 9.67–9.90 (1H, m), 9.90–10.10 (1H, m)

(31) Sodium

3-[4-(3-methyl-4,5-dihydro-3(2H)-oxo-1,2,4-triazin-6-yl)phenylcarbamoyl]propionate mp: 288° to 292° C. (dec.)
IR (Nujol): 3390, 3200, 1680, 1575 cm$^{-1}$
NMR (DMSO-d$_6$, δ): 1.17 (3H, d, J=6 Hz), Ca. 2.1–2.6 (4H, m), 4.3–4.7 (1H, m), Ca. 7.5 (1H, br. s), 7.54 (4H, s), 9.86 (1H, br s), 10.96 (1H, br s)

(32) Sodium

2-[4-(3-methyl-4,5-dihydro-3(2H)-oxo-1,2,4-triazin-6-yl)anilino]acetate mp: >230° C. (dec.)
NMR (DMSO-d$_6$, δ): 1.16 (3H, d, J=6.4 Hz), 3.38 (2H, s), 4.49 (1H; d, q; J=3, 6.4 Hz), 5.56 (1H, br s), 6.49 (2H, d, J=8 Hz), 7.29 (1H, br s), 7.37 (2H, d, J=8 Hz), 9.62 (1H, br s)
IR (Nujol): 3400, 3240, 1680, 1600, 1580, 1560 cm$^{-1}$

(33) Sodium 4-(5-methyl-4,5-dihydro-3(2H)-oxo-1,2,4-triazin-6-yl)oxanilate mp: >300° C.
NMR (DMSO-d$_6$, δ): 1.18 (3H, d, J=6.4 Hz), 4.36–4.79 (1H, m), 1H, br s), 7.60 (2H, d, J=9.2 Hz), 7.81 (2H, d, J=9.2 Hz), 9.87 (1H, br s), 10.25 (1H, br s)

(34)

6-[4-(2-Morpholinoacetamido)phenyl]-5-methyl-4,5-dihydro-1,2,4-triazin-3(2H)-one mp: 244° to 247° C.
NMR (DMSO-d$_6$, δ): 1.22 (3H, d, J=6.5 Hz), 2.39–2.72 (4H, m), 3.15 (2H, s), 3.53–3.86 (4H, m), 4.66 (1H; d, q; J=3.5, 6.5 Hz), 7.31–7.55 (1H, b.m.), 7.70 (4H, s), 9.73–10.13 (2H, m)

(35)

6-(4-Hydrazinophenyl)-5-methyl-4,5-dihydro-1,2,4-triazin-3(2H)-one hydrochloride mp: 235° C. (dec.)
NMR (DMSO-d$_6$, δ): 1.19 (3H, d, J=7.5 Hz), 4.45 (1H; d, q; J=3, 7.5 Hz), 7.02 (2H, d, J=8.5 Hz), 7.26–7.50 (1H, b.m.), 7.65 (2H, d, J=8.5 Hz), 7.9–9.0 (1H, b.m.), 9.8–10.0 (1H, b.m.) 9.7–10.9 (2H, b.m.)

(36)

6-[4-(4,5-Dihydro-3-methyl-5-oxopyrazol-1-yl)phenyl]-5-methyl-4,5-dihydro-1,2,4-triazin-3(2H)-one mp: 257° to 260° C. (dec.)
NMR (DMSO-d$_6$, δ): 1.24 (3H, d, J=6.5 Hz), 2.13 (3H, s), 3.66–3.78 (0.3H, m), 4.67 (1H, d, q; J=3.5, 6.5 Hz), 5.37 (0.85H, s), 7.31–7.56 (1H, m), 7.78 (4H, s), 9.94–10.07 (1H, m)

(37)

6-[4-(3,5-Dimethylpyrazol-1-yl)phenyl]-5-methyl-4,5-dihydro-1,2,4-triazin-3(2H)-one mp: 240° to 241° C.

NMR (DMSO-d$_6$, δ): 1.23 (3H, d, J=7 Hz), 2.17 (3H, s), 2.39 (3H, s), 4.69 (1H; d, q; J=3.5, 7 Hz), 6.09 (1H, s), 7.37–7.57 (1H, m), 7.53 (2H, d, J=9 Hz), 7.85 (2H, d, J=9 Hz), 10.02–10.15 (1H, m)

(38)

6-[4-(1H-Tetrazol-5-yl)phenyl]-5-methyl-4,5-dihydro-1,2,4-triazin-3(2H)-one mp: 153° to 183° C. (dec.)

NMR (DMSO-d$_6$, δ): 1.25 (3H, d, J=6.5 Hz), 4.76 (1H; d, q; J=3, 6.5 Hz), 7.44–7.64 (1H, b.m.), 7.95 (2H, d, J=8 Hz), 8.14 (2H, d, J=8 Hz), 10.1–10.3 (1H, b.m.)

(39)

6-[4-(4,5-Diethoxycarbonyl-1H-1,2,3-triazol-1-yl)-phenyl]-5-methyl-4,5-dihydro-1,2,4-triazin-3(2H)-one mp: 156° to 157.5° C.

NMR (DMSO-d$_6$, δ): 1.19 (3H, t, J=7 Hz) 1.29 (3H, d, J=6.5 Hz), 1.33 (3H, t, J=7 Hz), 4.34 (2H, q, J=7 Hz), 4.39 (2H, q, J=7 Hz), 4.74 (1H; d, q; J=3, 6.5 Hz), 7.42–7.67 (1H, m), 7.66 (2H, d, J=9 Hz), 7.99 (2H, d, J=9 Hz), 10.16–10.30 (1H, m)

(40)

6-[4-(1-Pyrrolyl)phenyl]-5-methyl-4,5-dihydro-1,2,4-triazin-3(2H)-one mp: 269° to 271° C.

NMR (DMSO-d$_6$, δ): 1.22 (3H, d, J=7 Hz), 4.71 (1H; d, q; J=3.2, 7 Hz), 6.28 (2H, t, J=2 Hz), 7.37–7.99 (3H, m), 7.58 (2H, d, J=9 Hz), 7.82 (2H, d, J=9 Hz), 9.97–10.15 (1H, b.m.)

(41)

6-[4-(3-Aminopropylamino)phenyl]-5-methyl-4,5-dihydro-1,2,4-triazin-3(2H)-one mp: 177.5° to 179° C.

NMR (DMSO-d$_6$, δ): 1.15 (3H, d, J=6 Hz), 1.59 (2H, t, J=6 Hz), 1.89 (2H, br s), 2.61 (2H, t, J=6 Hz), 2.8–3.3 (2H, m), 4.48 (1H, broad q, J=6 Hz), 5.89 (1H, broad t, J=5 Hz), 6.48 (2H, d, J=8 Hz), 7.20 (1H, br s), 7.36 (2H, d, J=8 Hz), 9.58 (1H, br s)

IR (Nujol): 3300, 3200, 1680, 1600 cm$^{-1}$ (42)

6-[4-(3-Ureidopropylamino)phenyl]-5-methyl-4,5-dihydro-1,2,4-triazin-3(2H)-one mp: 200° to 2.02.5° C. (dec.)

IR (Nujol): 3450, 3310, 3180, 1685, 1600 cm$^{-1}$

NMR (DMSO-d$_6$, δ): 1.16 (3H, d, J=6.4 Hz), 1.63 (2H, quintet, J=6.8 Hz), 2.8–3.3 (4, m), 4.49 (1H; d, q; J=3.6, 6.4 Hz), 5.36 (2H, br s), 5.8–6.2 (2H, broad m), 6.56 (2H, d, J=8.4 Hz), 7.19 (1H, br s), 7.45 (2H, d, J=8.4 Hz), 9.62 (1H, br s)

(43)

6-[4-(3-Morpholinopropionamido)phenyl]-5-methyl-4,5-dihydro-1,2,4-triazin-3(2H)-one mp: 145° to 149° C.

NMR (DMSO-d$_6$, δ): 1.21 (3H, d, J=6.9 Hz), Ca. 2.3–2.8 (8H, m), 3.47–3.74 (4H, m), 4.60 (1H; d, q; J=3.5, 6.9 Hz), 7.22–7.48 (1H, m), 7.63 (4H, s), 9.76–9.93 (1H, m), 10.04–10.20 (1H, m)

(44)

6-[4-(2-Oxo-1-pyrrolidinyl)phenyl]-5-methyl-4,5-dihydro-1,2,4-triazin-3(2H)-one mp: 278° to 280° C.

IR (Nujol): 3220, 3080, 1700 cm$^{-1}$

NMR (DMSO-d$_6$, δ): 1.19 (3H, d, J=7 Hz), Ca. 1.8–2.3 (2H, m), 2.49 (2H, t, J=6.6 Hz), 3.79 (2H, t, J=6.2 Hz), 4.57 (1H; d, q; J=3.2, 7 Hz), 7.33 (1H, br s), 7.63 (4H, s), 9.82 (1H, br s)

(45)

6-[4-(2-Oxoperhydropyrimidin-1-yl)phenyl]-5-methyl-4,5-dihydro-1,2,4-triazin-3(2H)-one mp: 304° to 306° C. (dec.)

IR (Nujol): 3200, 3060, 1690, 1645 cm$^{-1}$

NMR (DMSO-d$_6$, δ): 1.20 (3H, d, J=6.4 Hz), 1.8–2.2 (2H, m), Ca. 3.1–3.4 (2H, m), 3.64 (2H, 5, J=5.8 Hz), 4.62 (1H; d, q; J=2.6, 6.4 Hz), 6.61 (1H, br s), 7.31 (2H, d, J=9 Hz), Ca. 7.4 (1H, br s), 7.64 (2H, d, J=9 Hz), 9.91 (1H, br s)

(46)

6-[4-(2-Hydroxy-3-isopropylaminopropoxy)phenyl]-5-methyl-4,5-dihydro-1,2,4-triazin-3(2H)-one hydrochloride mp: 85° to 90° C.

IR (KBr): 3290 (broad), 1670, 1246, 1160 cm$^{-1}$

NMR (DMSO-d$_6$, δ): 1.15 (3H, d, J=6.2 Hz), 1.21 (6H, d, J=7 Hz), 3.07 (2H, m), 3.20 (1H, m), 3.90 (1H, m), 4.06 (2H, s), 4.60 (1H, m), 6.95 (2H, d, J=8.2 Hz), 7.64 (2H, d, J=8.2 Hz), 7.50 (1H, br s), 9.00 (2H, m), 9.83 (1H, br s)

(47)

6-[3-(2-Hydrazinocarbonylethyl)-4-methylamino)-phenyl]-5-methyl-4,5-dihydro-1,2,4-triazin-3(2H)-one mp: 238° to 239° C. (dec.)

IR (Nujol): 3400, 3300 (shoulder), 3200, 3080, 1690, 1665, 1625, 1605 cm$^{-1}$

NMR (DMSO-d$_6$, δ): 1.19 (3H, d, J=7 Hz), Ca. 2.2 to 2.7 (4H, m), 2.76 (3H, d, J=5 Hz), 4.17 (1H, s), 4.53 (1H; d, q; J=2, 7 Hz), 5.53 (1H, q, J=5 Hz), 6.49 (1H, d, J=9 Hz), Ca. 7.2 to 7.6 (2H, m), 8.96 (1H, br s), 9.65 (1H, br s)

(48)

6-(4-Glycylaminophenyl)-5-methyl-4,5-dihydro-1,2,4-triazin-3(2H)-one hydrochloride mp: 317° C. (dec.)

NMR (DMSO-d$_6$, δ): 1.20 (3H, d, J=6 Hz), Ca. 3.5–4.2 (2H, m), 4.62 (1H; d, q; J=3, 6 Hz), 7.43 (1H, br s), 7.71 (4H, s), 8.38 (2H, br s), 9.94 (1H, s), 11.10 (1H, s)

(49)

6-[4-[4-(2-Hydroxyethyl)piperazin-1-ylacetylamino]-phenyl]-5-methyl-4,5-dihydro-1,2,4-triazin-3(2H)-one mp: 230°–232° C. (dec.)

IR (Nujol): 3300, 3200, 3100, 1690 cm$^{-1}$

NMR (DMSO-d$_6$, δ): 1.22 (3H, d, J=7 Hz), 2.3–2.7 (10H, m), 3.13 (2H, s), 3.53 (2H, q, J=6 Hz), 4.33 (1H, t, J=6 Hz), 4.47–4.77 (1H, m), 7.4 (1H, br s), 7.71 (4H, s), 9.78 (1H, s), 9.93 (1H, br s)

(50)

6-[4-(N,N-Diisopropylglycyclamino)phenyl]-5-methyl-4,5-dihydro-1,2,4-triazin-3(2H)-one mp: 245° to 248° C. (dec.)

IR (Nujol): 3210, 3100, 1700 cm$^{-1}$

NMR (DMSO-d$_6$, δ): 1.04 (12H, d, J=7 Hz), 1.25 (3H, d, J=7 Hz), 2.85–3.25 (2H, m), 3.13 (2H, s), 4.67 (1H, dd, J=4 Hz, 7 Hz), 7.43 (1H, br s), 7.73 (4H, s), 9.67 (1H, s), 9.95 (1H, br s)

(51)

6-[4-(1-Pyrrolidinoacetylamino)phenyl]-5-methyl-4,5-dihydro-1,2,4-triazin-3(2H)-one mp: 231° to 233° C.

IR (Nujol): 3300, 1690, 1680, 1660 cm$^{-1}$

NMR (DMSO-d$_6$, δ): 1.21 (3H, d, J=7 Hz), 1.4–2.0 (4H, m), 2.3–2.7 (4H, m), 3.26 (2H, s), 4.4–4.76 (1H, m), 7.38 (1H, br s), 7.72 (4H, s), 9.80 (1H, s), 9.91 (1H, br s)

(52)

6-[4-(N,N-Dimethylglycylamino)phenyl]-5-methyl-4,5-dihydro-1,2,4-triazin-3(2H)-one mp: 228° to 230° C. (dec.)

IR (Nujol): 3300, 3200, 3100, 1690, 1620 cm$^{-1}$

NMR (DMSO-d$_6$, δ): 1.21 (3H, d, J=7 Hz), 2.29 (6H, s), 3.08 (2H, s), 4.62 (1H, d, q, J=3 Hz, 7 Hz), 7.38 (1H, br s), 7.68 (4H, s), 9.81 (1H, s), 9.91 (1H, br s)

(53)

6-(4-Lactoylaminophenyl)-5-methyl-4,5-dihydro-1,2,4-triazin-3(2H)-one mp: 217° to 225° C.

IR (Nujol): 3340, 3300, 3260, 1702, 1658, 1520, 1460, 1121 cm$^{-1}$

NMR (DMSO-d$_6$, δ): 1.20 (3H, d, J=7 Hz), 1.31 (3H, d, J=7 Hz), 3.95–4.37 (1H, m), 4.33–4.88 (1H, m), 5.70 (1H, d, J=5 Hz), 7.35 (1H, br s), 7.4–7.9 (4H, m), 9.69 (1H, s), 9.85 (1H, d, J=2 Hz)

(54)

6-[4-(2-L-Acetoxypropionylamino)phenyl]-5-methyl-4,5-dihydro-1,2,4-triazin-3(2H)-one mp: 232° to 241° C.

IR (Nujol): 3340, 3300, 3260, 1693, 1655, 1523, 1460, 1120 cm$^{-1}$

NMR (DMSO-d$_6$, δ): 1.19 (3H, d, J=6.8 Hz), 1.32 (3H, d, J=6.8 Hz), 3.87–4.45 (1H, m), 4.36–4.87 (1H, m), 5.69 (1H, d, J=5.0 Hz), 7.35 (1H, br s), 7.5–7.9 (4H, m), 9.72 (1H, s), 9.87 (1H, d)

EXAMPLE 37

The following compounds were obtained from 6-(4-aminophenyl)-5-methyl-4,5-dihydro-1,2,4-triazin-3(2H)-one or its derivatives according to a similar manner to that of Example 3,4,6-(1) or 9.

(1)

6-(4-n-Butylaminophenyl)-5-methyl-4,5-dihydro-1,2,4-triazin-3(2H)-one mp: 183° to 186.5° C. (from ethanol)

NMR (DMSO-d$_6$, δ): 0.7–1.9 (10H, m), 2.9–3.3 (2H, m), 4.54 (1H; d, q; J=3, 6 Hz), 5.95 (1H, t, J=5.6 Hz), 6.59 (2H, d, J=8.4 Hz), 7.25 (1H, b.s.), 7.49 (2H, d, J=8.4 Hz), 9.68 (1H, b.s.)

Anal. Calcd. for C$_{14}$H$_{20}$N$_4$O: C, 64.59; H, 7.74; N, 21.52; Found: C, 64.71; H, 7.71; N, 21.52

EXAMPLE 37-(2)

6-[4-(2-Hydroxyethylamino)phenyl]-5-methyl-4,5-dihydro-1,2,4-triazin-3(2H)-one.

mp: 182° to 185° C. (from 50% aqueous ethanol)

NMR (DMSO-d$_6$, δ): 1.15 (3H, d, J=6 Hz), 3.10 (2H, t, J=6 Hz), 3.53 (2H, t, J=6 Hz), 3.9–4.7 (3H, m), 6.55 (2H, d, J=8.8 Hz), 7.18 (1H, b.s.), 7.41 (2H, d, J=8.8 Hz), 9.58 (1H, b.s.)

EXAMPLE 37-(3)

6-[4-(3-Phthalimidopropylamino)phenyl]-5-methyl-4,5-dihydro-1,2,4-triazin-3(2H)-one.

NMR (DMSO-d$_6$, δ): 1.19 (3H, d, J=7 Hz), 1.91 (2H, quintet, J=7 Hz), 2.89–Ca. 3.3 (2H, m), 3.71 (2H, t, J=7 Hz), 4.54 (1H; d, q; J=3, 7 Hz), 5.96 (1H, t, J=5 Hz), 6.58 (2H, d, J=9 Hz), 7.25 (1H, b.s.), 7.48 (2H, d, J=9 Hz), 7.84 (4H, s), 9.69 (1H, b.s.)

EXAMPLE 37-(4)

6-(4-Benzylaminophenyl)-5-methyl-4,5-dihydro-1,2,4-triazin-3(2H)-one.

mp: 193° to 194° C. (recrystallized from ethanol)

NMR (DMSO-d$_6$, δ): 1.16 (3H, d, J=7 Hz), 4.31 (2H, d, J=6 Hz), 4.50 (1H; d, q; J=3.8, 7 Hz), 6.59 (2H, d, J=8.2 Hz), 6.61 (1H, b.s.), 7.3–7.6 (8 H, m), 9.69 (1H, b.s.)

EXAMPLE 37-(5)

6-(4-Ethoxycarbonylmethylaminophenyl)-5-methyl-4,5-dihydro-1,2,4-triazin-3(2H)-one.

mp: 180.5° to 182° C. (from ethanol)

NMR (DMSO-d$_6$, δ): 1.19 (3H, t, J=7 Hz), 1.17 (3H, d, J=6 Hz), 3.92 (2H, d, J=6 Hz), 4.13 (2H, q, J=7 Hz), 4.52 (1H; d, q; J=3.6, 6 Hz), 6.32 (1H, t, J=6 Hz), 6.57 (2H, d, J=8.6 Hz), 7.21 (1H, b.s.), 7.47 (2H, d, J=8.6 Hz), 9.66 (1H, b.s.)

IR (Nujol): 3400, 3280, 1740, 1650 cm$^{-1}$

Anal. Calcd. for C$_{14}$H$_{18}$N$_4$O$_3$: C, 57.92; H, 6.25; N, 19.30; Found: C, 57.93; H, 6.18; N, 19.40

EXAMPLE 37-(6)

6-[4-[N,N-Di(2-propynyl)amino]phenyl]-5-methyl-4,5-dihydro-1,2,4-triazin-3(2H)-one.

mp: 191° to 193° C.

NMR (DMSO-d$_6$, δ): 1.18 (3H, d, J=6.5 Hz), 3.14 (2H, t, J=2 Hz), 4.18 (4H, d, J=2 Hz), 4.59 (1H; d, q; J=3, 6.5 Hz), 6.94 (2H, d, J=9 Hz), 7.22–7.46 (1H, b.m.), 7.63 (2H, d, J=9 Hz), 9.66–9.9 (1H, b.m.)

Anal. Calcd. for C$_{16}$H$_{16}$N$_4$O: C, 68.55; H, 5.75; N, 19.99; Found: C, 68.44; H, 5.60; N, 20.19

EXAMPLE 37-(7)

6-[4-(2-Propynyl)aminophenyl]-5-methyl-4,5-dihydro-1,2,4-triazin-3(2H)-one.

mp: 221° to 224° C.

NMR (DMSO-d$_6$, δ): 1.17 (3H, d, J=7 Hz), 3.04 (1H, t, J=2 Hz), 3.90 (2H, d,d; J=2, 6 Hz), 4.54 (1H; d, q; J=3.5, 7 Hz), 6.32 (1H, t, J=6 Hz), 6.64 (2H, d, J=8.5 Hz), 7.12–7.36 (1H, b.m.), 7.50 (2H, d, J=8.5 Hz), 9.55–9.84 (1H, b.m.)

Anal. Calcd. for C$_{13}$H$_{14}$N$_4$O: C, 64.45; H, 5.82; N, 23.12; Found: C, 64.51; H, 5.82; N, 23.25

EXAMPLE 37-(8)

6-[4-(2-Pyridylamino)phenyl]-5-methyl-4,5-dihydro-1,2,4-triazin-3(2H)-one.

mp: 254° to 255° C. (dec.)

IR (Nujol): 3200, 3080, 1690, 1620 cm$^{-1}$

NMR (DMSO-d$_6$, δ): 1.22 (3H, d, J=7 Hz), 4.61 (1H; d, q; J=2, 7 Hz), 6.64–7.07 (2H, m), 7.33 (1H, b.m.), 7.43–7.91 (5H, m), 8.19 (1H; d,d; J=2, 5 Hz), 9.20 (1H, s), 9.80 (1H, b.m.)

Anal. Calcd. for C$_{15}$H$_{15}$N$_5$O: C, 64.04; H, 5.37; N, 24.89; Found: C, 64.23; H, 5.33; N, 24.97

EXAMPLE 37-(9)

6-[4-[2-(2-Methoxyethoxy)ethylamino]phenyl]-5-methyl-4,5-dihydro-1,2,4-triazin-3(2H)-one.

mp: 130° to 135° C.

NMR (DMSO-$d_6$, δ): 1.18 (3H, d, J=6.4 Hz), 3.1–3.4 (2H, m), Ca. 3.3 (3H, s), 3.4–3.8 (6H, m), 4.52 (1H; d, q; J=3, 6.4 Hz), 5.92 (1H, t, J=4 Hz), 6.60 (2H, d, J=8.4 Hz), 7.21 (1H, b.s.), 7.47 (2H, d, J=8.4 Hz), 9.63 (1H, d, J=1.4 Hz)

Anal. Calcd. for $C_{15}H_{22}N_4O_3$: C, 58.81; H, 7.24; N, 18.29; Found: C, 58.66; H, 7.00; N, 18.46

EXAMPLE 37-(10)

6-(4-Morpholinophenyl)-5-methyl-4,5-dihydro-1,2,4-triazin-3(2H)-one was obtained by reacting 6-(4-aminophenyl)-5-methyl-4,5-dihydro-1,2,4-triazin-3(2H)-one and 2,2'-bis(p-toluenesulfonyloxy)ethyl ether according to a similar manner to that of Example 4.

mp: 256° to 261° C.

NMR (DMSO-$d_6$, δ): 1.17 (3H, d, J=6.4 Hz), 2.9–3.4 (4H, m), 3.6–3.9 (4H, m), 4.53 (1H; d, q; J=3.4, 6.4 Hz), 6.86 (2H, d, J=9.4 Hz), 7.22 (1H, b.s.), 7.52 (2H, d, J=9.4 Hz), 9.68 (1H, d, J=2.2 Hz).

Anal. Calcd. for $C_{14}H_{18}N_4O_2$: C, 61.30; H, 6.61; N, 20.42; Found: C, 61.12; H, 6.51; N, 20.64

What is claimed is:

1. A compound of the formula:

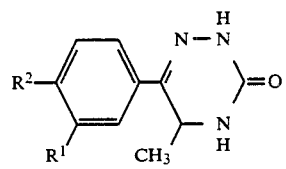

wherein
$R^1$ is hydrogen or halogen, and
$R^2$ is mono- or di-(lower)alkylamino, mono- or di-(lower)alkynylamino, mono- or di-(lower)alkylamino substituted by lower alkoxy, or a group of the formula —NH—CO—$R^4$ in which $R^4$ is lower alkyl substituted by a group selected from halogen, amino, hydroxy, lower alkanoyloxy and mono- or di-(lower)alkylamino, or its phermaceutically acceptable salt.

2. A compound of claim 1, wherein $R^2$ is a group of the formula

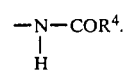

3. A compound of claim 2, wherein $R^4$ is lower alkyl substituted by hydroxy, halogen or amino.

4. A compound of claim 3, wherein $R^4$ is lower alkyl substituted by hydroxy.

5. The compound according to claim 4, which is 6-(4-lactoylaminophenyl)-5-methyl-4,5-dihydro-1,2,4-triazin-3(2H)-one.

6. A compound of claim 3, wherein $R^4$ is lower alkyl substituted by halogen.

7. The compound according to claim 6, which is 6-[4-(2-chloropropionylamino)phenyl]-5-methyl-4,5-dihydro-1,2,4-triazin-3(2H)-one.

8. A compound of claim 3, wherein $R^4$ is lower alkyl substituted by amino.

9. The compound according to claim 8, which is 6-(4-glycylaminophenyl)-5-methyl-4,5-dihydro-1,2,4-triazin-3(2H)-one.

10. A pharmaceutical composition comprising an effective amount of a compound of claim 1 for treating hypertension, thrombosis and (or) ulcer.

11. A method for treating hypertension, thrombosis and (or) ulcer which comprises administering a pharmaceutically effective amount of a compound of claim 1.

* * * * *